(12) United States Patent
Lesh

(10) Patent No.: US 6,471,697 B1
(45) Date of Patent: Oct. 29, 2002

(54) TISSUE ABLATION DEVICE AND METHOD

(75) Inventor: Michael D. Lesh, Mill Valley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/357,184

(22) Filed: Jul. 19, 1999

Related U.S. Application Data

(63) Continuation of application No. 08/853,861, filed on May 9, 1997, now Pat. No. 5,971,983.

(51) Int. Cl.⁷ .............................................. A61B 18/18
(52) U.S. Cl. ............................. 606/41; 606/46; 606/47; 607/101; 607/122
(58) Field of Search .............................. 606/41, 45, 46, 606/47; 600/585, 373–375, 377; 607/101, 122; 604/585

(56) References Cited

U.S. PATENT DOCUMENTS

| | | |
|---|---|---|
| 4,033,031 A | 7/1977 | Ballew |
| 4,117,836 A | 10/1978 | Erikson |

(List continued on next page.)

FOREIGN PATENT DOCUMENTS

| | | |
|---|---|---|
| DE | 296 09 350 | 8/1996 |
| DE | 195 37 084 | 4/1997 |

(List continued on next page.)

OTHER PUBLICATIONS

Avitall et al., "Physics and Engineering of Transcatheter Tissue Ablation", Journal of American College of Cardiology, 22(3):921–932 (1993).

Cox, J. et al., "The surgical treatment of atrial fibrillation-.I.Summary", Thoraci and Cardiovascular Surgery, 101(4):402–405 (1991).

Cox, J. "The surgical treatment of atrial fibrillation.IV.Surgical Technique", Thoracic and Cardiovascular Surgery, 101:(4):584–592 (1991).

(List continued on next page.)

*Primary Examiner*—Linda C. M. Dvorak
*Assistant Examiner*—David M. Ruddy
(74) *Attorney, Agent, or Firm*—John P. O'Banion; James C. Peacock, III

(57) ABSTRACT

A tissue ablation device creates long linear lesions along a body space wall of an animal, and primarily between adjacent pulmonary vein ostia in a left atrial wall. An ablation element includes first and second ends that are bordered by first and second anchors. The anchors are adapted to secure the ablation element ends at predetermined first and second locations along the body space wall such that the ablation element is adapted to ablate an elongate region of tissue between those locations. The anchors may be guidewire tracking members, each including a bore adapted to receive and track over a guidewire, and may anchor within adjacent pulmonary vein ostia when the engaged guidewires are positioned within the respective veins. Stop members may be provided on the guidewires and may be adapted for positioning the relative anchors or for forcing the anchors to fit snugly within the vein ostia. A conduit passageway through the catheter houses a stiffening stylet which may be advanced into the region of the ablation element in order to impart a shape to that element to conform it to a predetermined region of anatomy, or to stiffen the underlying catheter in order to advance the assembly into remote anatomy.

26 Claims, 21 Drawing Sheets

U.S. PATENT DOCUMENTS

| | | |
|---|---|---|
| 4,316,472 A | 2/1982 | Mirowski et al. |
| 4,411,266 A | 10/1983 | Cosman |
| 4,569,801 A | 2/1986 | Molloy et al. |
| 4,641,649 A | 2/1987 | Walinsky et al. |
| 4,660,571 A | 4/1987 | Hess et al. |
| 4,673,563 A | 6/1987 | Berne et al. |
| 4,699,147 A | 10/1987 | Chilson et al. |
| 4,762,129 A | 8/1988 | Bonzel |
| 4,841,977 A | 6/1989 | Griffith et al. |
| 4,882,777 A | 11/1989 | Narula |
| 4,898,591 A | 2/1990 | Jang et al. |
| 4,932,413 A | 6/1990 | Shockey et al. |
| 4,940,064 A | 7/1990 | Desai |
| 4,945,912 A | 8/1990 | Langberg |
| 4,976,711 A | 12/1990 | Parins et al. |
| 5,000,185 A | 3/1991 | Yock |
| 5,090,958 A | 2/1992 | Sahota |
| 5,104,393 A | 4/1992 | Isner et al. |
| 5,147,355 A | 9/1992 | Friedman et al. |
| 5,156,157 A | 10/1992 | Valenta, Jr. et al. |
| 5,195,990 A | 3/1993 | Weldon |
| 5,209,229 A | 5/1993 | Gilli |
| 5,228,442 A | 7/1993 | Imran |
| 5,231,994 A | 8/1993 | Harmjanz |
| 5,231,995 A | 8/1993 | Desai |
| 5,255,679 A | 10/1993 | Imran |
| 5,263,493 A | 11/1993 | Avitall |
| 5,281,215 A | 1/1994 | Milder |
| 5,293,868 A | 3/1994 | Nardella |
| 5,293,869 A | 3/1994 | Edwards et al. |
| 5,295,484 A | 3/1994 | Marcus et al. |
| 5,300,085 A | 4/1994 | Yock |
| 5,313,943 A | 5/1994 | Houser et al. |
| 5,324,284 A | 6/1994 | Imran |
| 5,342,292 A | 8/1994 | Nita et al. |
| 5,344,435 A | 9/1994 | Turner et al. |
| 5,345,936 A | 9/1994 | Pomeranz et al. |
| 5,348,554 A | 9/1994 | Imran et al. |
| 5,368,558 A | 11/1994 | Nita |
| 5,370,678 A | 12/1994 | Edwards et al. |
| 5,372,138 A | 12/1994 | Crowley et al. |
| 5,385,544 A | 1/1995 | Edwards et al. |
| 5,391,197 A | 2/1995 | Burdette et al. |
| 5,411,524 A | 5/1995 | Rahul |
| 5,423,808 A | 6/1995 | Edwards et al. |
| 5,423,811 A | 6/1995 | Imran et al. |
| 5,427,119 A | 6/1995 | Swartz et al. |
| 5,431,649 A | 7/1995 | Mulier et al. |
| 5,433,708 A | 7/1995 | Nichols et al. |
| 5,437,664 A | 8/1995 | Cohen et al. |
| 5,443,456 A | 8/1995 | Alliger et al. |
| 5,447,509 A | 9/1995 | Mills et al. |
| 5,456,682 A | 10/1995 | Edwards et al. |
| 5,474,530 A | 12/1995 | Passafaro et al. |
| 5,482,037 A | 1/1996 | Borghi |
| 5,484,400 A | 1/1996 | Edwards et al. |
| 5,487,385 A | 1/1996 | Avitall |
| 5,496,312 A | 3/1996 | Klicek |
| 5,496,346 A | 3/1996 | Horzewski et al. |
| 5,497,119 A | 3/1996 | Tedrow et al. |
| 5,497,774 A | 3/1996 | Swartz et al. |
| 5,501,227 A | 3/1996 | Yock |
| 5,505,702 A | 4/1996 | Arney |
| 5,509,900 A | 4/1996 | Kirkman |
| 5,522,873 A | 6/1996 | Jackman et al. |
| 5,545,161 A | 8/1996 | Imran |
| 5,545,193 A | 8/1996 | Fleischman et al. |
| 5,549,661 A | 8/1996 | Kordis et al. |
| 5,564,440 A | 10/1996 | Swartz et al. |
| 5,571,088 A | 11/1996 | Lennox et al. |
| 5,571,159 A | 11/1996 | Alt |
| 5,575,766 A | 11/1996 | Swartz et al. |
| 5,575,772 A | 11/1996 | Lennox |
| 5,575,788 A | 11/1996 | Baker et al. |
| 5,575,810 A | 11/1996 | Swanson et al. |
| 5,582,609 A | 12/1996 | Swanson et al. |
| 5,588,432 A | 12/1996 | Crowley |
| 5,606,974 A | 3/1997 | Castellano et al. |
| 5,607,422 A | 3/1997 | Smeets et al. |
| 5,607,462 A * | 3/1997 | Imran ........................ 607/122 |
| 5,617,854 A | 4/1997 | Munsif |
| 5,620,479 A | 4/1997 | Diederich |
| 5,630,837 A | 5/1997 | Crowley |
| 5,642,736 A | 7/1997 | Avitall |
| 5,645,082 A | 7/1997 | Sung et al. |
| 5,673,695 A | 10/1997 | McGee et al. |
| 5,674,274 A | 10/1997 | Morgan et al. |
| 5,676,662 A | 10/1997 | Fleischhacker et al. |
| 5,682,885 A | 11/1997 | Littman et al. |
| 5,683,445 A | 11/1997 | Swoyer |
| 5,685,322 A | 11/1997 | Sung et al. |
| 5,685,839 A | 11/1997 | Edwards et al. |
| 5,687,723 A | 11/1997 | Avitall |
| 5,687,729 A | 11/1997 | Schaetzle |
| 5,688,267 A | 11/1997 | Panescu et al. |
| 5,690,611 A | 11/1997 | Swartz et al. |
| 5,693,078 A | 12/1997 | Desai et al. |
| 5,697,925 A | 12/1997 | Taylor |
| 5,697,927 A | 12/1997 | Imran et al. |
| 5,702,438 A | 12/1997 | Avitall |
| 5,715,818 A | 2/1998 | Swartz et al. |
| 5,716,389 A | 2/1998 | Walinsky et al. |
| 5,718,241 A | 2/1998 | Ben-Haim et al. |
| 5,718,701 A | 2/1998 | Shai et al. |
| 5,720,775 A | 2/1998 | Larnard |
| 5,722,401 A | 3/1998 | Pietroski et al. |
| 5,722,403 A | 3/1998 | McGee et al. |
| 5,722,963 A | 3/1998 | Lurie et al. |
| 5,725,512 A | 3/1998 | Swartz et al. |
| 5,730,127 A | 3/1998 | Avitall |
| 5,730,704 A | 3/1998 | Avitall |
| 5,733,315 A | 3/1998 | Burdette et al. |
| 5,735,811 A | 4/1998 | Brisken |
| 5,735,846 A | 4/1998 | Panescu et al. |
| 5,741,249 A | 4/1998 | Moss et al. |
| 5,741,320 A | 4/1998 | Thornton et al. |
| 5,743,870 A | 4/1998 | Edwards |
| 5,743,903 A | 4/1998 | Stern et al. |
| 5,755,663 A | 5/1998 | Larsen et al. |
| 5,755,664 A | 5/1998 | Rubenstein |
| 5,755,715 A | 5/1998 | Stern et al. |
| 5,755,760 A | 5/1998 | Maguire et al. |
| 5,769,846 A | 6/1998 | Edwards et al. |
| 5,782,239 A | 7/1998 | Webster, Jr. |
| 5,782,898 A | 7/1998 | Dahl et al. |
| RE35,880 E | 8/1998 | Waldman et al. |
| 5,797,842 A | 8/1998 | Pumares et al. |
| 5,797,877 A | 8/1998 | Hamilton et al. |
| 5,797,903 A | 8/1998 | Swanson et al. |
| 5,797,905 A | 8/1998 | Fleischman et al. |
| 5,800,378 A | 9/1998 | Edwards et al. |
| 5,800,379 A | 9/1998 | Edwards |
| 5,800,413 A | 9/1998 | Swartz et al. |
| 5,800,428 A | 9/1998 | Nelson et al. |
| 5,800,432 A | 9/1998 | Swanson |
| 5,807,249 A | 9/1998 | Qin et al. |
| 5,807,308 A | 9/1998 | Qin et al. |
| 5,807,391 A | 9/1998 | Wijkamp |
| 5,807,395 A | 9/1998 | Mulier et al. |
| 5,840,031 A | 11/1998 | Crowley |
| 5,840,076 A | 11/1998 | Swanson et al. |

| | | | |
|---|---|---|---|
| 5,842,984 A | 12/1998 | Avitall | |
| 5,843,154 A | 12/1998 | Osypka | |
| 5,846,218 A | 12/1998 | Brisken et al. | |
| 5,885,278 A | 3/1999 | Fleischman | |
| 5,938,660 A | 8/1999 | Swartz et al. | |
| 5,971,983 A | 10/1999 | Lesh | |
| 6,024,740 A | 2/2000 | Lesh et al. | |
| 6,064,902 A | 5/2000 | Haissaguerre et al. | |
| 6,071,279 A | 6/2000 | Whayne et al. | |
| 6,071,281 A | 6/2000 | Burnside et al. | |
| 6,071,282 A | 6/2000 | Fleischman | |
| 6,117,101 A | 9/2000 | Diederich et al. | |
| 6,214,002 B1 | 4/2001 | Fleischman et al. | |

FOREIGN PATENT DOCUMENTS

| | | |
|---|---|---|
| WO | WO 93/00958 | 1/1993 |
| WO | WO 93/08755 | 5/1993 |
| WO | WO 93/16632 | 9/1993 |
| WO | WO 93/20767 | 10/1993 |
| WO | WO 93/20770 | 10/1993 |
| WO | WO 93/20886 | 10/1993 |
| WO | WO 94/00050 | 1/1994 |
| WO | WO 94/21165 | 9/1994 |
| WO | WO 94/21167 | 9/1994 |
| WO | WO 94/21168 | 9/1994 |
| WO | WO 95/05781 | 3/1995 |
| WO | WO 95/10318 | 4/1995 |
| WO | WO 95/10319 | 4/1995 |
| WO | WO 95/10321 | 4/1995 |
| WO | WO 95/15115 | 6/1995 |
| WO | WO 95/19738 | 7/1995 |
| WO | WO 96/10961 | 10/1995 |
| WO | WO 96/00036 | 1/1996 |
| WO | WO 96/10961 | 4/1996 |
| WO | WO 96/26675 | 9/1996 |
| WO | WO 96/32885 | 10/1996 |
| WO | WO 96/32897 | 10/1996 |
| WO | WO 97/32525 | 9/1997 |
| WO | WO 97/37607 | 9/1997 |
| WO | WO 97/45156 | 12/1997 |
| WO | WO 98/02201 | 1/1998 |

OTHER PUBLICATIONS

Diederich et al., "Induction of Hyperthermia Using Intracavitary Multielement Ultrasonic Applicator", IEEE: Transactions on Biomedical Engineering 36(4)432–438 (Apr. 1989).

Diederich et al., "The development of intracavitary ultrasonic applicators for hyperthermia: A design and experimental study", Med. Phys. 17(4):626–634 (Jul/Aug. 1990).

Haissagurre et al., "Right and Left Atrial Radiofrequency Catheter Therapy of Paroxysmal Atrial Fibrillation", Journal of Cardiovascular Electrophysiology, 7(12):1132–1144 (1996).

Hindricks et al., "Catheter Ablation", Current Management of Arrhythmias, pp. 373–378 (1991).

Lesh, M., "Interventional Electrophysiology–State of the Art", American Heart Journal, 216(3):686–698 (1993).

Jais et al., "Biatrial Dimensions Relevant to Catheter Abalation," North American Society of Pacing and Electrophysiology, 17th Annual Scientific Sessions, Abstract Form.

\* cited by examiner

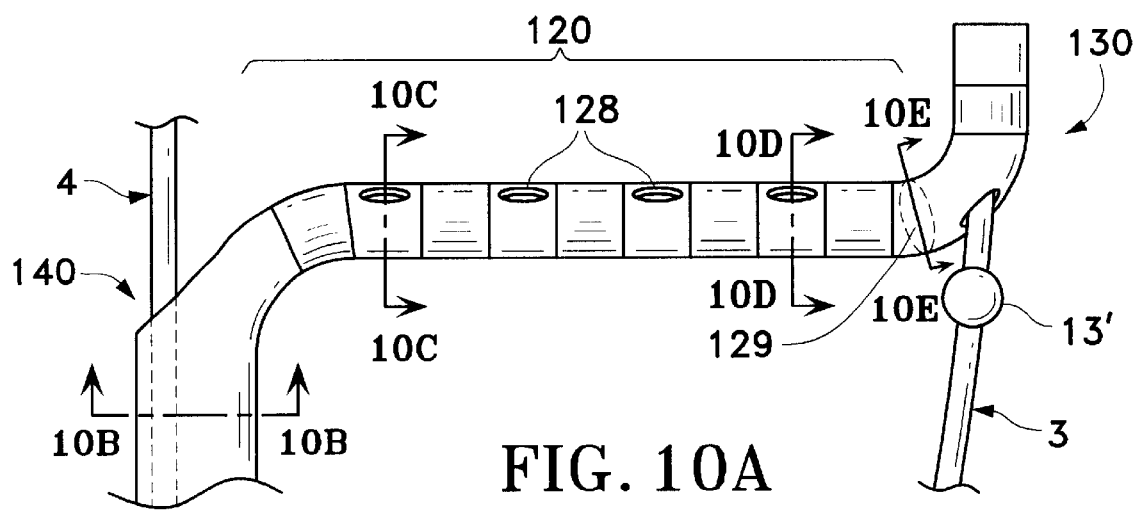
FIG. 10A
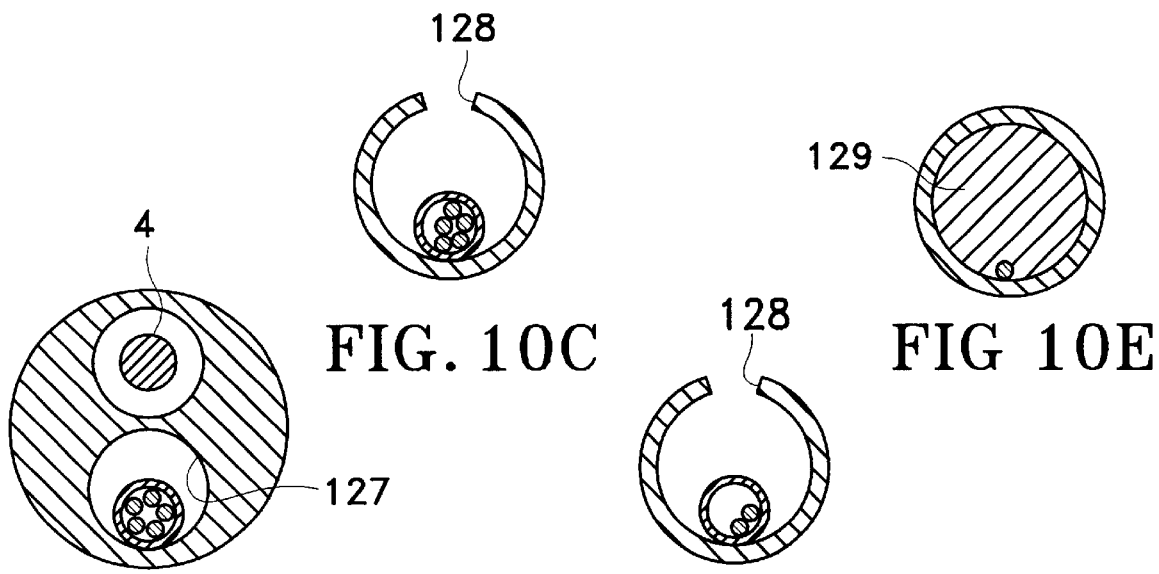
FIG. 10C
FIG. 10E
FIG. 10B
FIG. 10D
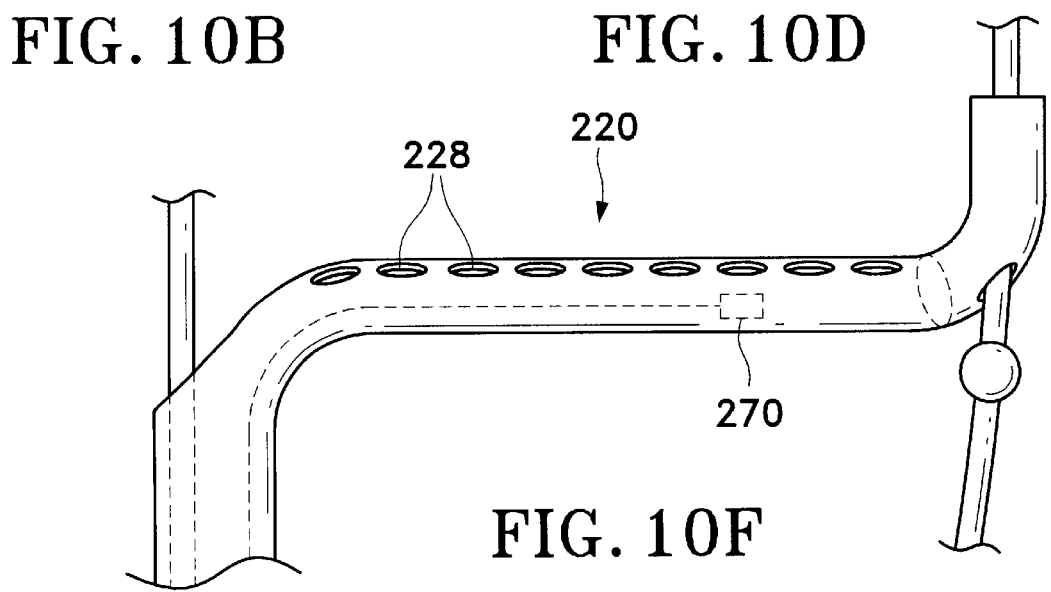
FIG. 10F

TISSUE ABLATION DEVICE AND METHOD

CROSS-REFERENCE TO RELATED APPLICATIONS

This application is a continuation of application Ser. No. 08/853,861 filed on May 9, 1997 now U.S. Pat. No. 5,971,983.

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

1. Field of the Invention

The present invention is a surgical device. More particularly, it is a medical catheter assembly that has an ablation element which is adapted to have its two ends anchored at predetermined locations on a body space wall such that the ablation element is adapted to firmly contact the length of tissue between predetermined locations for the purpose of forming a long linear lesion therebetween.

2. Description of the Background Art

Atrial Fibrillation

Cardiac arrhythmias, and atrial fibrillation in particular, remain a persistent medical condition in modern society. In the United States alone, approximately 1% of the total adult population is afflicted by atrial fibrillation, currently more than 2.5 million people, with prevalence increasing as a function of age. The resulting loss of blood flow due to incomplete cardiac contractions along with a rapid heart rate can lead to shortness of breath, dizziness, limited physical endurance, and chest pains. Persistence of atrial fibrillation renders an individual susceptible to congestive heart failure, stroke, other thromboembolic events, and myocardial ischemia. Considerable information is evolving regarding the conditions of the heart which contribute to the appearance of atrial fibrillation, factors which may be exacerbated by stress, anxiety, high blood pressure, heart valve disorders, and heart muscle dysfunction. An initial overview of the clinical phenomena associated with atrial arrhythmia is as follows.

The mammalian heart is composed of three different categories of cardiac tissue namely, atrial, ventricular, and excitatory conduction types. Normally, the atrial and ventricular muscles of the heart are electrically excited in a synchronous, patterned fashion. The cardiac cycle commences with the generation of action potentials by the sino-atrial (SA) node, located in the lateral wall of the right atrium. These action potentials propagate through the atrial chamber, possibly along preferential conduction pathways leading to the atrioventricular (AV) node. Potentials emanating from the AV node travel through the His-Purkinje bundle to the ventricular tissue, causing a synchronous contraction of the ventricles following that of the atria.

Pathological conditions of the cardiac tissue may lead to asynchronous cardiac rhythms, resulting in an overall elevation in the heart rate, inclusive of paroxysmal or chronic tachycardias. Tachycardias may initiate in the AV node, the bundle of His, or more generally in the atrial or ventricular tissues. The aforementioned tachycardias may manifest as a multiwavelet reentrant mechanism, resulting in asynchronous eddies of electrical impulses scattered about the atrial chamber. The fibrillation may also be more focal in nature, caused by the rapid, repetitive firing of an isolated center within the atria, but so rapidly that the remainder of the atrium cannot follow in a synchronized fashion.

Presently, many categories of tachycardia may be detected using the electrocardiogram (EKG). An alternative, more sensitive procedure commonly used to detect localized aberrations in electrical activity, and thus confirm the presence of arrhythmias such as atrial fibrillation, is the mapping of the cardiac chambers as disclosed in U.S. Pat. Nos. 4,641,649 and 4,699,147 and WO 96/32897.

Numerous cardiac arrhythmias, such as atrial fibrillation, were once thought untreatable except by pharmacological or surgical intervention, both capable of manifesting undesirable side effects. Recently, the emergence of less invasive catheter ablation methods have expanded the field of cardiac electrophysiology to provide limited percutaneous solutions to the medical conditions just described. A brief description of the aforementioned conventional therapies for atrial fibrillation and approaches to cardiac ablation thereof is found below.

Regimes of Conventional Treatment

Episodes of tachycardia may be responsive to treatment by antiarrhythmic medication, as disclosed in U.S. Pat. No. 4,673,563 to Berne et al. and further described in U.S. Pat. No. 4,569,801. In addition, pharmacological intervention for treating atrial arrhythmias has been disclosed in the Hindricks, et al. in "Current Management of Arrhythmias" (1991). However, the administration of such medications sometimes does not restore normal cardiac hemodynamics, and may ultimately exacerbate the arrhythmic condition through the occurrence of proarrhythmia.

Specific clinical circumstances may necessitate invasive surgical intervention for multiwavelet tachycardias, including the placement of implantable atrial defibrillators to maintain sinus rhythms as disclosed in U.S. Pat. Nos. 4,316,472; 5,209,229; 5,411,524 or alternatively, by the mechanical destruction of atrial electrical conduction pathways, as described by Cox, J L et al. in "The surgical treatment of atrial fibrillation. I. Summary" *Thoracic and Cardiovascular Surgery* 101 (3), pp. 402–405 (1991) or Cox, J L "The surgical treatment of atrial fibrillation. IV. Surgical Technique", *Thoracic and Cardiovascular Surgery* 101 (4), pp. 584–592 (1991).

Described by the Cox procedure, as referenced above, is a strategy to incur patterned surgical incisions within the atrial chambers, creating a maze by which propagating electrical waves are extinguished at the lines of suture. In this way, reentrant wavelets are not sustained, arrhythmia cannot persist, and normal sinus rhythm is restored. Curative efforts for atrial arrhythmias were initially focused on the right atrium, with mixed results. However, procedures which combine right and left atrial treatments have been observed to have dramatically increased success rates. In the left atrium, a common protocol includes vertical incisions from the two superior pulmonary veins and terminating just posterior to the mitral valve annulus, transversing the inferior pulmonary veins en route. An additional horizontal line also connects the superior ends of the two vertical incisions. Thus, the region of the pulmonary vein ostia is isolated from the other atrial tissue. By severing electrical conduction pathways within the atrial tissues, the fibrillatory process is eliminated.

Transcatheter Cardiac Ablation

Alternative, less invasive approaches have recently been adopted for the treatment of cardiac arrhythmias in a clinical setting. These catheter-based transvascular approaches include procedures and associated devices for the treatment of ventricular or supraventricular tachycardias, as described in Lesh, MD in "Interventional Electrophysiology—State of the Art, 1993" American Heart Journal, 126, pp. 686–698 (1993).

The initial approach to the ablative procedure used catheters responsive to high energy direct current (DC) to either disrupt the AV node function or to create a heart block by disruption of the His bundle. However, it has been more recently observed that radio frequency (RF) is often a more desirable energy source as disclosed in WO 93/20770. Alternative ablation techniques have also been disclosed. For example, an ablative catheter responsive to microwave frequencies is described in WO 93/20767. Other catheter based ablation technologies which have also been disclosed to render the aberrant cells electrically silent include freezing, ultrasound, and laser energy as disclosed in U.S. Pat. Nos. 5,147,355; 5,156,157 and 5,104,393, respectively.

Ablation procedures have typically involved the incremental application of electrical energy to the endocardium to form focal lesions to interrupt the inappropriate conduction pathways. Methods and devices for using percutaneous ablative techniques intended to remedy cardiac fibrillation or arrhythmias have been disclosed in U.S. Pat. Nos. 5,231,995; 5,487,385; WO 94/21165 and WO 96/10961 in addition to U.S. Pat. Nos. 5,228,442 and 5,324,284 to Imran. The disclosures of these references are herein incorporated in their entirety by reference thereto.

For some types of cardiac arrhythmias, a focal ablative lesion (i.e., 5–8 mm in diameter) is adequate to sever inappropriate conduction pathways such as those associated with the Wolff-Parkinson-White syndrome. However, such focal lesions are not appropriate for most cases of atrial fibrillation which involve multiple reentrant loops. These excitation waves would simply go around a focal ablative lesion. Thus, as in the surgical "maze" procedure, long linear lesions are required in order to segment the atrium to block the wave fronts associated with most forms of atrial fibrillation.

Certain particular catheter based technologies exist which are intended to emulate all or a portion thereof, the incision patterns of the maze procedure using curvilinear catheters. The use of such catheters in ablative procedures is disclosed in Avitall et al., in "Physics and Engineering of Transcatheter Tissue Ablation", Journal of American College of Cardiology, Volume 22, No. 3:921–932 (1993). In addition, the use of transcatheter ablation to remedy atrial fibrillation in a clinical setting, specifically by the use of a percutaneously introduced ablation catheter (with either a 7F deflectable 4-mm tip with thermocoupler; Cordis Webster, Miami, Fla., or a woven Dacron 14 by 4-mm multielectrode from Bard Electrophysiology, Tewksbury, Mass.) is described in Haissaguerre, et al. in "Right and Left Atrial Radiofrequency Catheter Therapy of Paroxysmal Atrial Fibrillation" in Journal of Cardiovascular Electrophysiology 7(12), pp. 1132–1144 (1996). These articles are herein incorporated in their entirety by reference thereto.

The aforementioned references disclose methods which use a sequential application of energy from a point on a catheter, which is remotely manipulated, to ostensibly create an ablation maze according to a predetermined pattern. However, this process may fail to produce continuous, transmural lesions, thus leaving the opportunity for the reentrant circuits to reappear. In addition, minimal means are available in these embodiments for steering the catheters to anatomic sites of interest such as the pulmonary veins.

Catheter Positioning Technology

Many different types of catheters have been disclosed for guiding, accessing, and positioning at a predetermined location within the body for the purposes of performing a medical treatment.

A number of steerable catheter systems, exhibiting a plurality of curvatures at their distal end, have been devised which may be introduced into the blood vasculature or other lumen, navigating the many passageways, ultimately reaching previously inaccessible areas within the cardiac chamber without invasive surgery. For example, catheters with complex curvatures and preshaped member loops have been devised for placement in the cardiac chambers as described in U.S. Pat. Nos. 4,117,836 (left coronary artery); 5,195,990 (aorta); the right ventricle in U.S. Pat. No. 4,882,777; U.S. Pat. No. 4,033,031 discloses a catheter design for access of the pericardial space. Additional examples of intravascular steerable catheters used in cardiac ablative procedures are disclosed in U.S. Pat. Nos. 4,898,591 and 5,231,994. The disclosures of these references are herein incorporated in their entirety by reference thereto.

One class of catheters exemplifies steerable guidewires as rails. Of these, some are "over-the-wire" types of catheters which have lumens substantially extending along their entire length and which are adapted to track over a guidewire. Other "guidewire tracking"-types of catheters have also been disclosed, generally referred to "rapid-exchange" or "monorail" catheters, which have only a distal region of the catheter length adapted to track over a guidewire. This type of catheter benefits in the ability to separately control proximal regions of both the guidewire and also the catheter externally of the body, since only the distal region of the catheter is coaxial over the guidewire. Examples of these types of catheters are disclosed in U.S. Pat. Nos. 5,300,085 and 5,501,227 to Yock.

Furthermore, the use of particular guiding sheath designs for use in ablation procedures in both the right and/or left atrial chambers are disclosed in U.S. Pat. Nos. 5,427,119; 5,497,119; 5,564,440; 5,575,766 to Swartz et al. In particular, the aforementioned art describes a method which requires a real time repositioning of a point source of energy along a preferred pathway in the moving wall of a beating atrium. In doing so, a remote percutaneous manipulation of the device is required using only the means of Xray fluoroscopy for visualizing catheter location. Moreover, the use of a monorail catheter with several deployable shapes for the purposes of creating incremental lesions along a predetermined linear path in the right atrium, accomplished by sustaining the elongate ablation element at a predetermined location along a body space wall, is disclosed in U.S. Pat. No. 5,487,385 to Avitall.

Several catheter designs have also incorporated a plurality of distally located mechanisms to stabilize the catheter, thus enabling precise placement of the ablation electrodes within a cardiac chamber. Such technologies may include the use of a stop and/or a balloon as disclosed in U.S. Pat. Nos. 5,487,385 and 5,496,346, respectively, along the guidewire contained in the catheter. Alternatively, a catheter adapted to be mechanically retained in a fixed position within a vessel lumen is disclosed in U.S. Pat. No. 5,509,500 to Kirkman. Furthermore, the positioning of a catheter within the heart using a distally located inflatable balloon device during ablation procedures has been disclosed in U.S. Pat. No. 5,571,159 to Alt and U.S. Pat. No. 4,762,129 to Bonzel.

None of the cited references discloses a tissue ablation device having an ablation element having anchors at each of two ends for anchoring the ends to first and second predetermined locations along a body space wall in order to secure the length of the ablation element to the tissue between those locations for ablating a long linear lesion.

None of the cited references discloses a kit of multiple ablation catheters, each having a unique ablation length which may be chosen for use in the formation of a long linear lesion between two anatomic anchoring points, such as the two pulmonary vein ostia, according to the measured length of the distance between those anatomic sites in a patient.

None of the cited references discloses a catheter having a means for selectively positioning an intermediate region of the catheter located proximally of the distal tip, nor do they disclose a catheter having a guidewire tracking region with both proximal and distal guidewire ports positioned on that intermediate catheter region.

In addition, none of the cited references discloses a catheter device that provides a multirail guidewire tracking capability at various positions along the catheter length.

Still further, none of the cited references discloses a tissue ablation device assembly having an elongate ablation element with at least one suctioning port along its length which is coupled to a suction source in order to anchor the ablation element to tissue along a body space wall.

BRIEF SUMMARY OF THE INVENTION

The present invention is a medical device assembly for creating long linear lesions in a body space wall which defines at least in part a body space in an animal.

One aspect of the invention is an ablation catheter assembly which includes an elongate body having proximal and distal end portions and an ablation element on the distal end portion that is adapted to ablate tissue when coupled to an ablation actuator. The ablation element has first and second ends. A first anchor is positioned adjacent the first end and is adapted to secure the first end at a predetermined first location along the body space wall. A second anchor is positioned adjacent the second end and is adapted to secure the second end at a predetermined second location along the body space wall.

By securing the first and second ends of the ablation element in this variation to the predetermined locations with the anchors, the ablation element is adapted to substantially contact a length of tissue adjacent to the ablation element and between the first and second locations without substantially repositioning the distal end portion of the elongate body.

In one variation of this assembly, at least one of the first and second anchors is a guidewire tracking member which has a bore that is adapted to advance the adjacent end of the ablation element over a guidewire and into an ostium of a pulmonary vein along a left arterial wall when the guidewire is positioned within that vein. Further to this variation, when both anchors are guidewire tracking members, the ablation element may be anchored at each of its ends over wires in adjacent pulmonary vein ostia and is adapted to substantially contact and ablate a region of arterial wall tissue extending between those adjacent ostia.

In a further variation of this assembly, a radially enlarged stop member is provided on at least one of the guidewires. When the stop member is positioned distally on the wire relative to the guidewire tracking member, it provides a preselected position against which the guidewire tracking member may be advanced. When the stop member is positioned proximally on the wire relative to the guidewire tracking member, the guidewire may be used to push the stop against the proximal port of the guidewire tracking member to thereby force the guidewire tracking member snugly into the pulmonary vein.

Another aspect of the invention is a kit of ablation catheters for creating long linear lesions in the tissue of a body space wall which at least in part defines a body space in an animal. This kit includes in packaged combination a plurality of ablation catheters, each having a proximal end portion, a distal end portion, and an ablation element in the region of the distal end portion. The ablation element of each ablation catheter has first and second ends which are each bordered by an anchor adapted to secure the adjacent end to a predetermined location along a body space wall. Furthermore, the ablation element of each ablation catheter has a different length than the ablation element of the other ablation catheters. An ablation catheter having an ablation element with a particular length may be chosen from this kit based upon the measured distance between adjacent pulmonary vein ostia in a patient's left atrial wall.

Another aspect of the invention is a medical device assembly which is adapted for positioning multiple portions thereof at multiple predetermined locations within a body space of an animal. This assembly includes an elongate body having a proximal end portion, a distal end portion, and an intermediate guidewire tracking member located between the proximal and distal end portions. The intermediate guidewire tracking member forms an intermediate bore with first and second intermediate bore ends. The bore is adapted to slideably receive a guidewire through the first intermediate bore end from a position externally of the elongate body and to direct the guidewire to extend from the second intermediate bore end also externally of the elongate body.

In one variation of this assembly, an ablation element is provided on the distal end portion and has a proximal end that is adjacent to the intermediate guidewire tracking member. In another variation of this assembly, a guidewire is provided which has a radially enlarged stop member which is adapted to engage the bore of the intermediate guidewire tracking member and limit the movement of the guidewire relative to that bore.

Another aspect of the invention is a method for positioning an intermediate guidewire tracking member of an elongate body of a medical device assembly at a predetermined location within a body space. The intermediate guidewire tracking member forms a bore which is adapted to receive a guidewire and which is located between a proximal end portion and a distal end portion of the elongate body. The method includes the steps of: (1) inserting a guidewire into the bore in the region of the intermediate portion from a position externally of the elongate body; (2) advancing the guidewire through the bore; and (3) extending the guidewire from the bore and externally of the elongate body in the region of the intermediate portion.

Another aspect of the invention is a method for creating a long linear lesion in the tissue between first and second predetermined locations along the surface of a body space wall. The method includes the steps of: (1) measuring the distance between the first and second predetermined locations; (2) choosing a medical device assembly having an ablation element with first and second length having a predetermined length based upon the measured distance; (3) anchoring the first and second ends of the ablation element at the first and second predetermined locations; and (4) ablating the tissue between the first and second predetermined locations to form a long linear lesion therebetween.

Another aspect of the current invention is a method for creating long linear lesions in a tissue wall which defines at least a portion of a body space. This method uses a medical device that has an elongate body with a distal end portion that includes an ablation element adapted to ablate tissue adjacent thereto when coupled to an ablation actuator. This method includes the steps of: (1) securing a first end of the ablation element at a first location along the tissue wall; (2) securing a second end of the ablation element at a second location along the tissue wall; and (3) activating the ablation element with the ablation actuator to ablate tissue adjacent thereto.

BRIEF DESCRIPTION OF THE DRAWINGS

The invention will be more fully understood by reference to the following drawings which are for illustrative purposes only:

FIG. 10A shows an exploded partial perspective view of a further variation of the atrial lesioning device assembly shown in FIG. 7, and shows a series of fluid ports located along the length of the ablation element.

FIGS. 10B–E show sequential cross-sectional views of the ablation element shown in FIG. 10A, taken along lines 10B—10B; 10C—10C; 10D—10D; and 10E—10E, respectively.

FIG. 10F shows an exploded partial perspective view of yet a further variation for the ablation element region of the ablation device assembly shown in FIG. 10A.

DETAILED DESCRIPTION OF THE INVENTION

Figure 1:
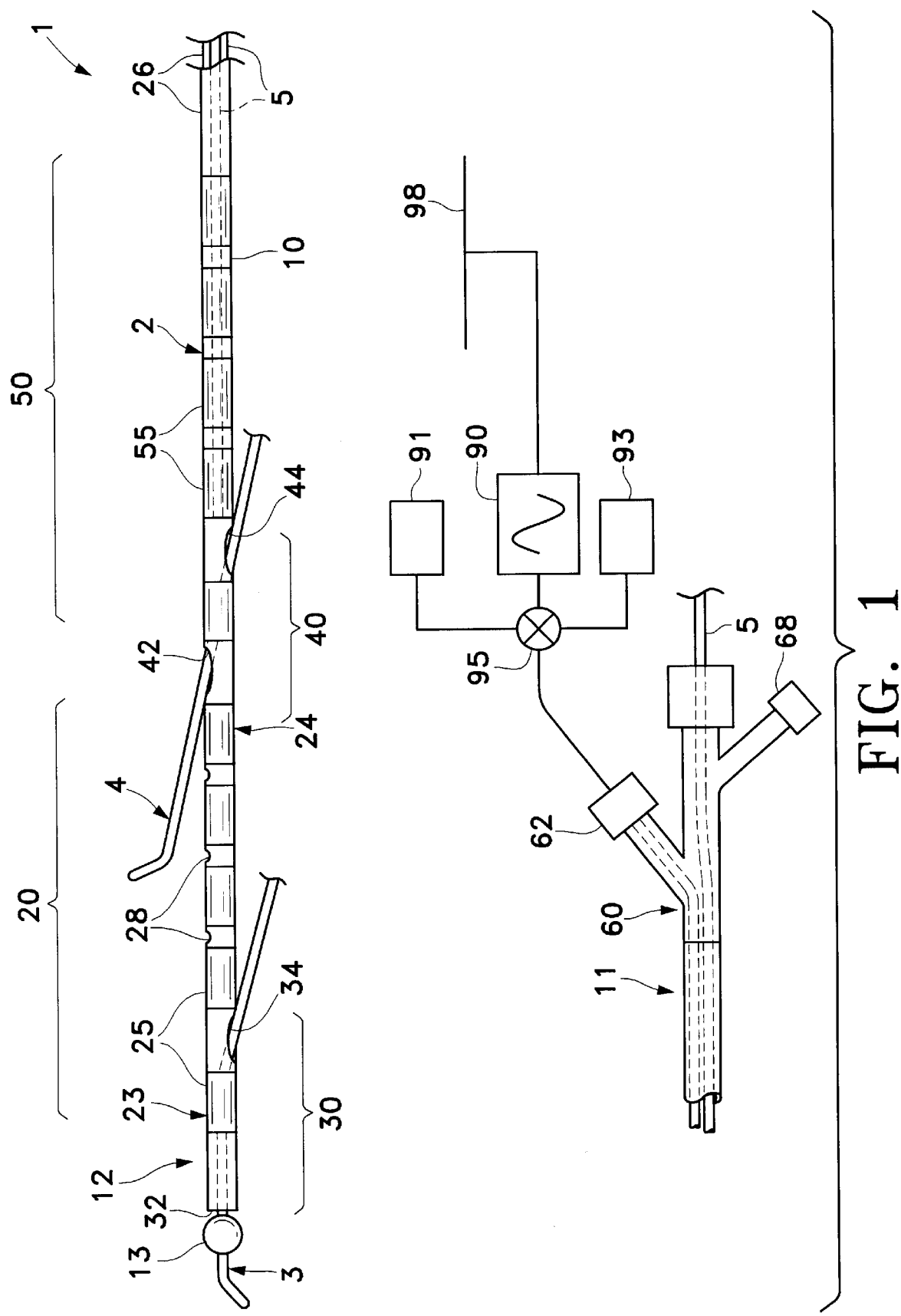
FIG. 1 is a perspective view of one atrial lesioning catheter assembly of the present invention.

The present invention is herein described by reference to particularly desirable embodiments shown in the figures. However, the present invention broadly provides an elongate ablation element with anchors at multiple regions of that element, such as at each of its ends, which allow those ends to be secured at predetermined locations along a body space wall, such as along an atrial wall. In this novel arrangement, the ablation element is adapted to firmly contact a continuous length of tissue along the body space wall between the predetermined locations to form a long linear lesion in that tissue.

The term "anchor" is herein intended to mean an element which is at least in part located in an anchoring region of the device and which is adapted to secure that region at a predetermined location along a body space wall. As such, "anchor" is intended to provide fixation as a securing means over and above a mere normal force against a single tissue surface which is created by confronting contact between the device and the tissue. Examples of suitable "anchors" within the intended meaning include (but are not limited to): an element that directly engages the tissue of the wall at the predetermined location such as by clamping, suctioning, or penetrating that tissue; and a guidewire engaging or tracking member which provides a bore or lumen adapted to track a guidewire through an ostium of a lumen extending from the body space wall, thereby penetrating the plane of the body space wall at a predetermined location at the ostia.

Furthermore, an expandable element, such as an expandable balloon or cage, is considered an anchor to the extent that it radially engages at least two opposite body space wall portions to secure the expandable element in place (such as opposite sides of a vessel). To the extent that the disclosure of the invention below is directed to any one particular anchoring element, it is contemplated that other variations and equivalents such as those described may also be used in addition or in the alternative to that particular element.

The phrase "ablation element" is herein intended to mean an element which is adapted to substantially ablate tissue in a body space wall upon activation by an actuator.

The term "ablation" or derivatives thereof is herein intended to mean the substantial altering of the mechanical, electrical, chemical, or other structural nature of the tissue. In the context of intracardiac ablation applications as shown and described with reference to the embodiments below, "ablation" is intended to mean sufficient altering of the tissue properties to substantially block conduction of electrical signals from or through the ablated cardiac tissue.

The term "element" within the context of "ablation element" is herein intended to mean a discrete element, such as an electrode, or a plurality of discrete elements, such as a plurality of spaced electrodes, which are positioned so as to collectively ablate an elongated region of tissue.

Therefore, an "ablation element" within the intended meaning of the current invention may be adapted to ablate tissue in a variety of ways. For example, one suitable "ablation element" may be adapted to emit energy sufficient to ablate tissue when coupled to and energized by an energy source. Suitable examples of energy emitting "ablation elements" within this meaning include without limitation: an electrode element adapted to couple to a direct current (DC) or alternating current (AC) source, such as a radiofrequency (RF) current source; an antenna element which is energized by a microwave energy source; a heating element, such as a metallic element which is energized by heat such as by convection or current flow, or a fiber optic element which is heated by light; a light emitting element, such as a fiber optic element which transmits light sufficient to ablate tissue when coupled to a light source; or an ultrasonic element such as an ultrasound crystal element which is adapted to emit ultrasonic sound waves sufficient to ablate tissue when coupled to a suitable excitation source.

More detailed descriptions of radiofrequency (RF) ablation electrode designs which may be suitable in whole or in part as the ablating element according to the present invention are disclosed in U.S. Pat. No. 5,209,229 to Gilli; U.S. Pat. No. 5,487,385 to Avitall; and WO 96/10961 to Fleischman et al. More detailed descriptions of other energy emitting ablation elements which may be suitable according to the present invention are disclosed in U.S. Pat. No. 4,641,649 to Walinsky et al. (microwave ablation); and U.S. Pat. No. 5,156,157 to Valenta, Jr. et al. (laser ablation). The disclosures of these patents are herein incorporated in their entirety by reference thereto.

In addition, other elements for altering the nature of tissue may be suitable as "ablation elements" within the intended meaning of the current invention. For example, a cryoblation probe element adapted to sufficiently cool tissue to substantially alter the structure thereof may be suitable. Furthermore, a fluid delivery element, such as a discrete port or a plurality of ports which are fluidly coupled to a fluid delivery source, may be adapted to infuse an ablating fluid, such as a fluid containing alcohol, into the tissue adjacent to the port or ports to substantially alter the nature of that tissue. More detailed examples of cryoblation or fluid delivery elements such as those just described are disclosed in U.S. Pat. No. 5,147,355 to Friedman et al. and WO 95/19738 to Milder, respectively. The disclosures of these patents are incorporated in their entirety by reference thereto.

It is also to be further appreciated that the various embodiments shown and described in this disclosure collectively provide one beneficial mode of the invention, which mode is specifically adapted for use in the left atrium of a mammal. In this mode, the elongate ablation element is adapted to have its ends anchored in adjacent pulmonary vein ostia in the left atrium, with the elongate ablation element in substantial contact with the tissue that spans the length between those ostia. By subsequent ablation of the tissue between anchors in the adjacent ostia, a long linear lesion is created and provides a conduction block to electrical flow across the length of the lesion.

As will be appreciated from the more detailed disclosure of the embodiments below, a pattern of multiple long linear lesions between adjacent pulmonary vein ostia, and also including portions of the mitral valve annulus and septum, may be completed with the present invention. One pattern of such multiple ablation lesions can be considered a "box" of isolated conduction within the region of the pulmonary veins, and is believed to provide a less-invasive improvement and less traumatic alternative to the invasive "maze" surgical procedure previously described.

FIG. 1 shows one variation of the present invention wherein a tissue ablation device assembly (1) is shown to include an ablation catheter (2) which has an elongate body (10) with a proximal end portion (11) and a distal end portion (12). Distal end portion (12) is shown to include an ablation element (20) which is bordered on each of two ends (23,24) by distal and intermediate guidewire tracking members (30,40), respectively.

The anchors of the variation shown in FIG. 1 are provided by the distal and intermediate guidewire tracking members (30,40). These guidewire tracking members are generally shown in FIG. 1 to be slideably engaged over distal and proximal guidewires (3,4), respectively, to form a "multi-rail" catheter system. Guidewire (3) is further shown to include a stop (13) that is radially enlarged with a diameter which is larger than the diameter of the first distal guidewire port (32). The stop (13) provides one positioning means for placing the distal guidewire tracking member (30) at a predetermined location along the guidewire to anchor it in that position in the anatomy, as will be more readily apparent by reference to FIG. 3 below. In addition to the use of the stop mechanism shown, other structures may be employed to provide relative positioning of the catheter over the guidewire, such as by use of an expandable member on the guidewire to internally engage the guidewire tracking lumen, as would be apparent to one of ordinary skill.

Ablation element (20) is shown in the variation of FIG. 1 to include a plurality of electrodes (25) which are variously positioned along the length of the elongate body (10). A second ablation element (50) is also shown to include a second plurality of electrodes (55). As will be developed in more detail with regard to FIGS. 11–15B below, the electrodes of these ablation elements are adapted via electrode leads to at least one ablation actuator and also to instruments which are adapted to monitor intercardiac electrical signals and to artificially pace cardiac contractile rhythm via the electrodes. In the variation shown, a common bundle of electrode leads (26) couple the various electrodes to the proximal coupler (60).

In general, any of several designs for coupler (60) may be suitable for use with the present invention, as would be apparent to one of ordinary skill. In the variation shown in FIG. 1, proximal coupler (60) engages proximal end portion (11) of the elongate body (10) of ablation catheter (2). Proximal coupler (60) includes a hemostatic valve (61) which is shown to slideably engage and provide fluid integrity around stylet (5). An electrical coupler (62) is also included, which is schematically shown selectively coupled to ablation actuator (90), signal recording device (91), and pacing device (93). Still further, a hydraulic coupler (68) is also shown and is fluidly coupled to fluid ports (28) for purposes of suction or fluid delivery.

Ablation actuator (90) is engaged to both electrical coupler (62) and also to a ground patch (98). A circuit is thereby created which includes the ablation actuator (90), the ablation element (20), the patient's body (not shown), and the ground patch (98) which provides either earth ground or floating ground to the current source. In this circuit, an electrical current, such as a radiofrequency ("RF") signal may be sent through the patient between the electrode element and the ground patch, as would be apparent to one of ordinary skill.

Ablation Element Anchors

Further detail regarding the anchors shown at distal and proximal guidewire tracking members (30,40) in FIG. 1 is provided as follows. Distal guidewire tracking member (30) includes a distal lumen (not shown) which extends between a first distal guidewire port (32) in the catheter tip and a second distal guidewire port (34) located proximally of the first distal guidewire port. Intermediate guidewire tracking member (40) is positioned on an intermediate portion of the elongate body of the catheter and includes an intermediate lumen (not shown) which extends between a first intermediate guidewire port (42) and a second intermediate guidewire port (44) located proximally of the first intermediate guidewire port.

Therefore, each of the guidewire tracking members (30, 40) shown in FIG. 1 is adapted to receive the respective guidewire through its lumen such that the guidewire extends externally of the catheter's elongate body on either side of the region of slideable engagement. This arrangement, however, is merely one example of a broader functional structure of the guidewire tracking variation illustrated by the anchors of FIG. 1. Considering this variation more generally, bores are formed at each of the distal and intermediate regions of the elongate body. Each bore is adapted to track over a guidewire separately and independently of the other bore. Each bore generally has two open ends or ports, and the respectively engaged guidewire extends through the bore and externally of the device from each bore end.

Therefore, according to the general structure just described, the specific guidewire tracking member embodiments of FIG. 1 may be modified according to one of ordinary skill without departing from the scope of the invention. For example, a cuff or looped tether of material may be provided at the desired anchoring location along the elongate body and thereby form a bore that is adapted to circumferentially engage a guidewire according to the description above. More particularly, a metallic ring, or a polymeric ring such as polyimide, polyethylene, polyvinyl chloride, fluoroethylpolymer (FEP), or polytetrafluoroethylene (PTFE) may extend from the elongate body in a sufficient variation. Or, a suitable strand of material for forming a looped bore for guidewire engagement may also be constructed out of a filament fiber, such as a Kevlar or nylon filament fiber. One more specific example of such an alternative guidewire tracking member which may be suitable for use in the current invention, particularly as a distal guidewire tracking member, is disclosed in U.S. Pat. No. 5,505,702 to Arney. The disclosure of that reference is herein incorporated in its entirety by reference thereto.

Further to the intermediate guidewire tracking member (40) of FIG. 1, a means is beneficially provided by that member for positioning and anchoring an intermediate region of an elongate catheter body at a predetermined location within a body space. The embodiment shown in FIG. 1 allows the engaged guidewire to traverse the radial axis of the elongate body, entering on one side of the catheter and exiting on the other. This embodiment may be constructed in a variety of ways, including, for example, the more specific embodiments provided collectively in FIGS. 2A–E.

Figure 2A:
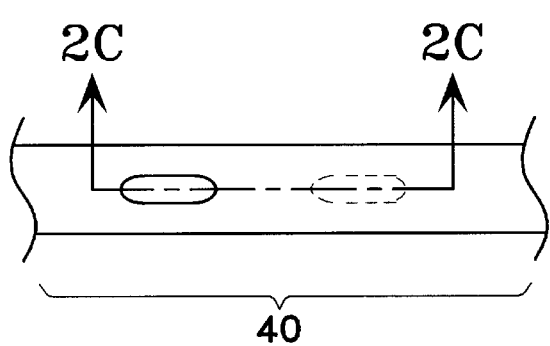
FIGS. 2A–B show partial exploded top and side perspective views, respectively, of the intermediate guidewire tracking member of the catheter assembly shown in FIG. 1.
Figure 2B:
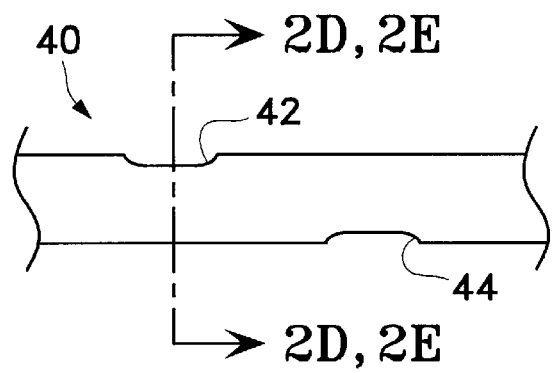
Figure 2C:
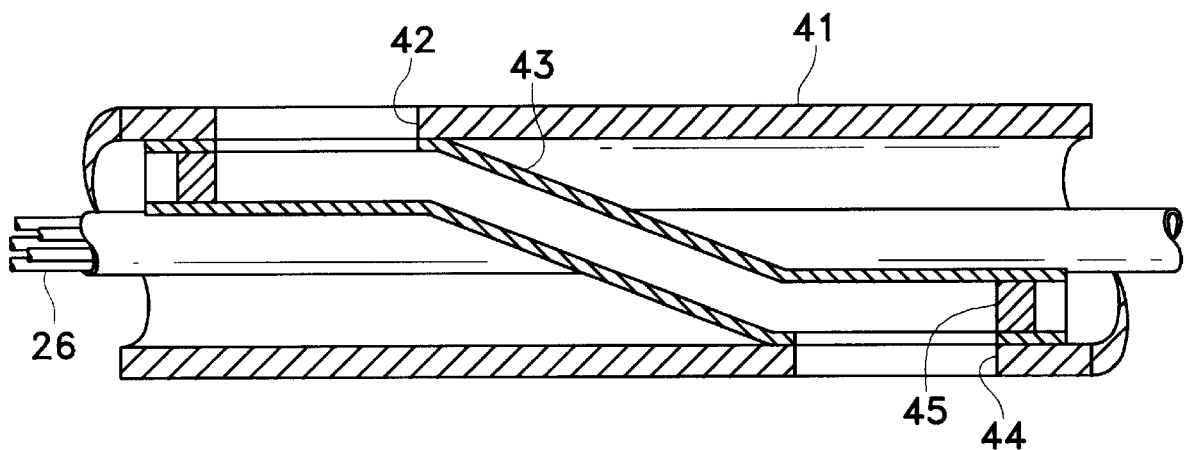
FIGS. 2C–D show a side sectional view and a cross sectional view of one variation for the intermediate guidewire tracking member, taken along lines 2C—2C from FIGS. 2A and 2D—2D from FIG. 2B, respectively.
Figure 2D:
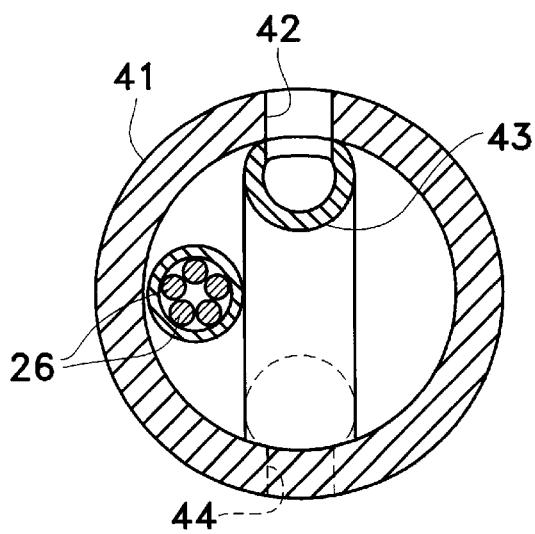

FIGS. 2C–D show an outer tubing (41) which coaxially surrounds an inner guidewire tubing (43). Guidewire tubing (43) is adhered to either side of the internal wall of the outer tubing (41). In one method, this may be accomplished by extending a shaped metallic mandrel within the interior lumen of the guidewire tubing (43) which forces that tubing against the wall of the outer tubing at preferred locations where ports are desired. By subsequently heating the region or regions of contact, such as by induction heating of the mandrel, the guidewire and outer tubings may melt together. This melt bond procedure may be performed simultaneously at each tubing interface or in series. After melting the tubings together and subsequent cooling, the mandrel is withdrawn.

Apertures are formed at the melted tubing interfaces such as by laser or mechanical drilling (either before or after withdrawal of the mandrel). Optionally, the ends of the inner tubing on the outer border of each formed port may be blocked, such as by filling the cross section of tubing in that region with adhesive or further melting a plug of similar material in that region (45), as would be apparent to one of ordinary skill.

The structure shown in FIGS. 2C–D allows for the required guidewire tracking lumen and also maintains at least one additional, longitudinal conduit through the region of the guidewire tracking lumen between the guidewire tubing (43) and the outer tubing (41). This allows for the passage of electrode leads (26), and may also provide for additional elements to communicate therethrough, such as for slideably advancing stylets therethrough or for suction/fluid delivery, as will be discussed in more detail below.

Figure 2E:
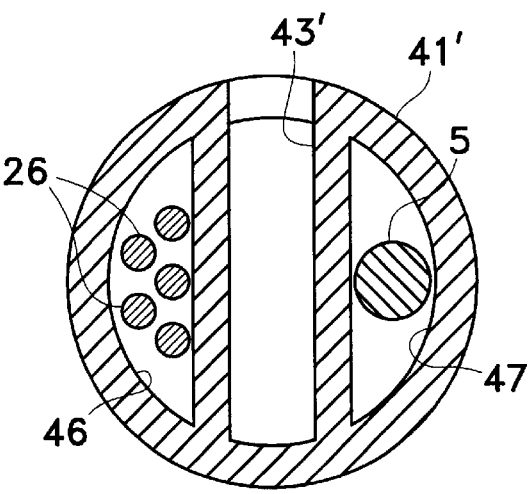
FIG. 2E shows a cross sectional view of another variation for the intermediate guidewire tracking member shown in FIG. 2B and is taken along lines 2E—2E.

FIG. 2E shows a further embodiment for intermediate guidewire tracking member (40), wherein a multi-lumen extruded tubing (41') includes a central lumen as the guidewire lumen (43'). Guidewire lumen (43') is bordered on either side by a first lumen, shown as electrode lead lumen (46), and a second lumen (47) which has varied additional functionality as just described for FIGS. 2C–D, including suctioning, fluid delivery, and passage of stylets for remote manipulation of distal catheter regions. In this embodiment, first and second intermediate guidewire ports (42,44) may be formed at the same longitudinal position along the elongate catheter body, rather than in staggered proximal-distal arrangement. In this design, a guidewire may slideably engage the tracking member in a perpendicular plane to the longitudinal axis of the elongate body.

Figure 3:
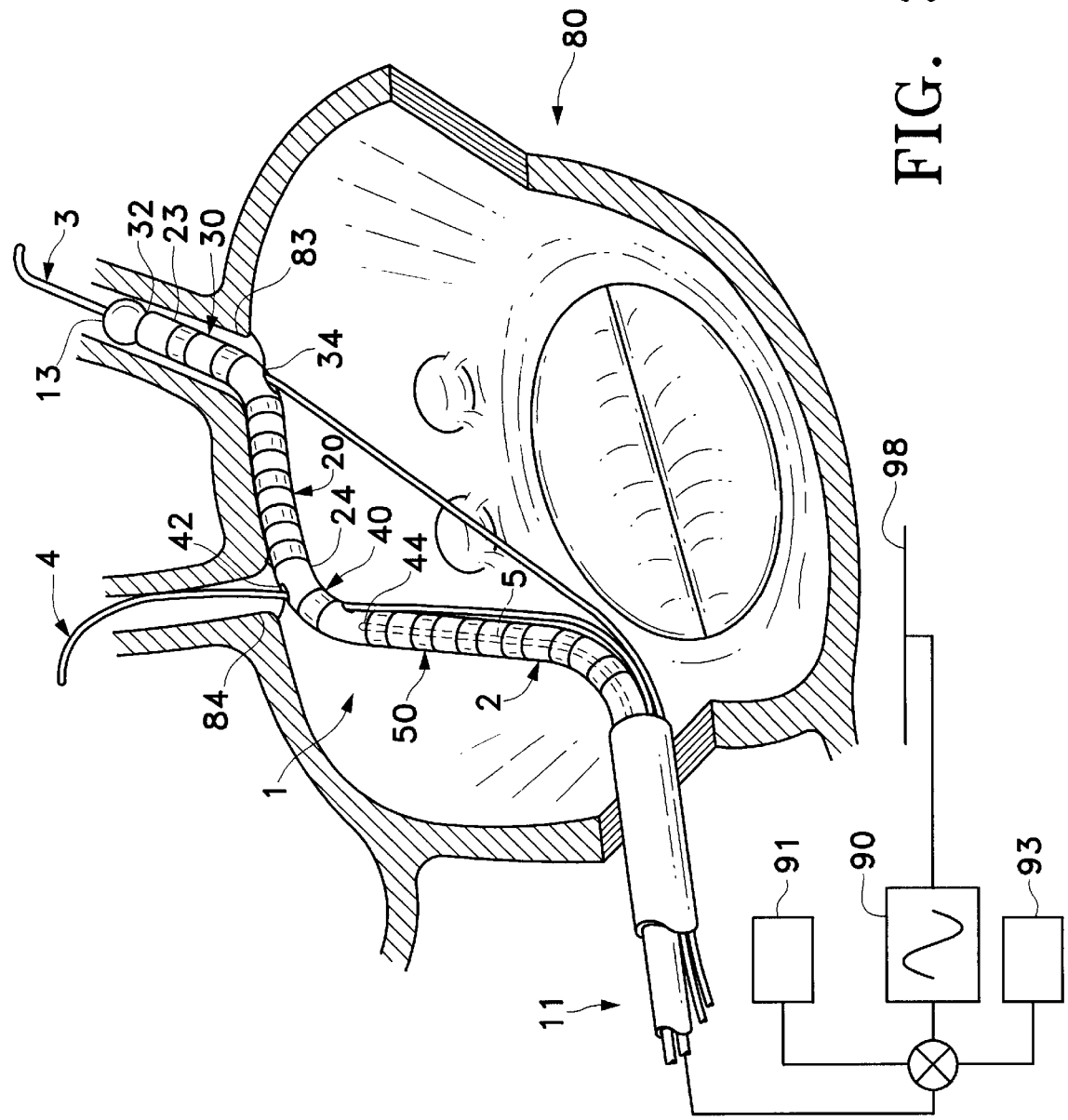
FIG. 3 shows a perspective view of the atrial lesioning catheter assembly of FIG. 1, shown in use with two opposite ends of an ablation element anchored in adjacent left and right superior pulmonary vein ostia along a left atrial wall and prior to forming a long linear lesion between those ostia.

FIG. 3 further shows tissue ablation device assembly (1) in use during the formation of a long linear lesion between adjacent pulmonary vein ostia in a left atrium (80). In this Figure (and further regarding the alternative variations shown in FIGS. 4–9) the ablation catheter (2) is shown with the distal and intermediate guidewire tracking members (30,40) in the left and right superior pulmonary vein ostia (83,84), respectively. This particular arrangement is provided merely for the purpose of illustrating the operation of the anchoring mechanisms which are beneficially provided with the long linear lesioning device of the current invention. The proximal end portion (11) of the elongate body is further shown throughout FIGS. 3–9C in schematic view in order to illustrate engagement of the ablation element to ablation actuator (90), which is further schematically shown coupled to a return electrode (98), and also to signal recording device (91) and pacing device (93).

FIG. 3 initially shows two guidewires (3,4) which have been previously placed within the left and right pulmonary veins through their corresponding ostia (83,84) via transeptal sheath (6). This guidewire positioning may be accomplished by virtue of the steerability and resultant sub-selectability of the guidewires, themselves, within the atrial chamber. In addition or in the alternative, enhanced guiding systems such as that disclosed in U.S. Pat. No. 5,575,766 to Swartz et al. may also be used to enhance the positioning of each guidewire into the desired vein ostia.

Suitable guidewires for use in the present invention may vary, and previously known guidewire designs for placing other catheter device assemblies within the internal body spaces of the anatomy may be suitable for many applications. In general, these guidewires have a metallic core, such as a stainless steel core or a superelastic metallic core, including a nickel-titanium core, which tapers distally and includes a radiopaque coil soldered, welded, or brazed over the tapered region.

Furthermore, commonly known guidewires having an outer diameter of at least 0.014", including those having an outer diameter of approximately 0.018" or 0.032", may be suitable. The guidewires should also be either pre-shaped or shapeable in their distal tip region, and should also be torqueable and radiopaque (such as by the radiopaque coils just described), such that the device may be manipulated to sub-select the pulmonary vein ostia in the atrium under Xray fluoroscopy. In any event, the guidewires should be of suitable construction in order to provide sufficient support and steerability to position and guide the catheter assembly of the present invention into the pulmonary vein ostia within the atrium, as would be apparent to one of ordinary skill.

Stop (13) is a radial enlargement which may be formed as a separate member over the underlying guidewire construction. Stop (13) may be made for example by soldering a ball of solder onto the outer surface of the underlying wire. Stop (13) may also be a polymeric member, such as that chosen from the group of polymers consisting of polyethylene, polyurethane, polyvinyl chloride, or the like. Furthermore, an enlarged region of adhesive such as a cyanoacrylate adhesive may be formed over the guidewire to form the stop (13).

Once placed in the respective ostia, each of the guidewires (3,4) provides an initial platform over which a region of the ablation catheter assembly engaged with the guidewire may be positioned for anchoring at the respective vein ostia. FIG. 3 shows the distal end portion of ablation catheter (2) after it has been advanced in a beneficial arrangement over the two guidewires (3,4). Each of the distal and intermediate guidewire tracking members (30,40) is coaxially engaged over guidewires (3,4), respectively, according to the following exemplary procedure.

After the guidewire distal end portions are positioned in vivo as described, the guidewire proximal end portions (not shown) may be "backloaded" into the respective distal and intermediate guidewire lumens of the catheter assembly. This is done by inserting the guidewire proximal end into for example the first distal guidewire port (32), and then retrogradedly advancing that guidewire proximal end rearwardly through the distal lumen and out the second distal guidewire port (34).

Once the guidewires (3,4) and guidewire tracking members (30,40) are respectively engaged, the ablation catheter (2) is advanced over the guidewires (3,4) and into the region of their respective distal end portions in the internal body space. The distal end portion of ablation catheter (2) is advanced with respect to guidewire (3) until first distal guidewire port (32) confronts stop (13) within the first pulmonary vein, as shown in FIG. 3. With stop (13) positioned in a predetermined location along pulmonary vein with respect to ostium (83), the confronting engagement with distal guidewire tracking member (30) selectively positions the distal end (23) of the ablation element at a desired location within the ostium.

Second distal guidewire port (34) is actually shown in FIG. 3 to be located within the distal region of ablation element (20), and is positioned in the space between adjacent ablation electrodes. In this arrangement, the region of coaxial coupling between guidewire (3) and the second distal guidewire port (34) may be positioned at or proximal to the pulmonary vein ostium, while a portion of the ablation element (20) may still be positioned within the ostium. It is believed that, for the purposes of forming efficacious conduction blocks in the regions of the left atrial pulmonary vein ostia, the long linear lesions should extend between and include at least the base of the pulmonary veins adjacent the ostia.

In addition to anchoring distal end (23) of the ablation element (20) in a first pulmonary vein ostium (83) as just described, proximal end (24) is anchored in the region of the adjacent right superior pulmonary vein ostium (84) by coaxially advancing intermediate guidewire tracking member (40) over guidewire (4).

Subsequent to positioning and anchoring each of the ends of ablation element (20), the ablation element is thereby adapted at least in part to substantially and firmly contact the length of tissue between the ablation element ends, including a linear region of tissue between the ostia and also portions of the ostia and veins stemming therefrom (at least at the first ostia). By energizing the electrodes along the anchored ablation element, the adjacent tissue is ablated to form a long linear lesion between the predetermined anchoring locations at the ostia.

It may also be desirable according to this invention to position a third portion of the device at a third predetermined location along the body space wall. For example, a second ablation element (50) is shown variously throughout the figures to be positioned on the ablation catheter (2) proximally of the ablation element (20). Second ablation element (50) has its distal end anchored in the vicinity of the second predetermined anchoring location within the right superior pulmonary vein ostia via intermediate guidewire tracking member (40).

A third anchoring or positioning means may be provided in order to position the proximal end of the second ablation element (50) at the third predetermined location to allow for another long linear lesion to be formed in a predetermined orientation and pattern along the atrial wall relative to the first lesion formed by the first ablation element. For example, stylet (5) is adapted to function in this positioning role and is shown in shadowed view variously throughout the figures within the region of the second ablation element (50). The stylet (5) is engaged within a stylet lumen (not shown) within the elongate body and is adapted to remotely manipulate the positioning of the ablation catheter (2) at the third location.

The construction of the stylet used in the various embodiments of the invention may vary, and is determined by the particular performance needs of a specific application. A suitable stylet may be a metal mandrel, such as a stainless steel mandrel or a superelastic metallic mandrel (for example, a nickel-titanium mandrel), which is slideably advanceable within a proximal lumen of the ablation catheter. The stylet may also be coated with a lubricious coating, such as with a fluoroethylpolymer (FEP), polytetrafluoroethylene (PTFE), paralene, or a hydrophilic polymeric coating, in order to facilitate slideable manipulation of the stylet within the stylet lumen of the elongate body.

Further, the stylet should generally have a length adapted such that the distal end may be placed at the required region of the ablation catheter for in vivo positioning while the stylet proximal end extends externally of the body and the assembly to allow for remote manipulation by a physician user at its proximal extremity. Still further, the stylet should be preshaped in its distal end region, such that torsion on the proximal extremity of the stylet is adapted to controllably and translumenally manipulate the stylet tip in order to position the coaxially engaged catheter shaft along the atrial wall surface.

Further to the beneficial "catheter manipulating" role of the stylet just described, only one anchor may be necessary in some circumstances to achieve firm contact with a body space wall along the length of an elongate ablation element. By anchoring one end of the ablation element at a first predetermined location, such as in a pulmonary vein ostia, the shaped stylet may be used to position the other end or portion at a second predetermined location. In this manner, the first anchor provides a focus about which the stylet's manipulation may sweep the other portion of the ablation element, much like a compass may be used to sweep an arc or position a point about that arc at a predetermined location relative to the first location of the focus.

Stylet (5) may also be adapted to advance further distally within the catheter, particularly during in vivo placement and anchoring of the distal guidewire tracking member at the first anchoring location. In one particular variation, the region of the elongate body which houses the ablation element may be designed to be particularly flexible, such as for the purpose of conforming to the atrial wall anatomy. This flexibility may, however, sacrifice pushability and the ability to advance and remotely manipulate the distal end portion within the body space. Therefore, the variable positioning and use of the stylet within this distal catheter region may allow for the requisite stiffness to track, position, and anchor the ablation element when the stylet is advanced within that region, and allow also for flexible conformity of the ablation element to the atrial wall when the stylet is proximally withdrawn.

As would be apparent to one of ordinary skill, stylet (5) is also shown in shadowed view variously throughout the rest of the figures and is intended to perform similar functions in the variations of those figures as those just described.

Further to the "third location" positioning feature just described, a third anchor may also be provided on the device, such as proximally of the second ablation element (50) shown in FIGS. 1 and 3. For example, a "proximal guidewire tracking member" (not shown) similar to the intermediate guidewire tracking member embodiments described may be provided as a third anchor adjacent to the proximal end of the second ablation element. By engaging that third anchor to an additional guidewire, for example, the proximal guidewire tracking region may be positioned and anchored over the additional guidewire in yet a third ostium, such as the right inferior pulmonary vein ostium according to the device positioning shown in FIG. 3.

As would be apparent to one of ordinary skill, additional anchors and/or ablation elements may also be provided along the elongate body in combination with those just described. For example, additional proximal guidewire tracking members may be provided, or additional stylets may slideably engage the interior lumens of the device elongate body, for the purpose of positioning other proximal portions of the elongate body within the anatomy.

In one particular mode not shown, a plurality of ablation elements may be positioned between all adjacent pairs of vein ostia by use of a desirably positioned plurality of anchors along the elongate body which are adapted to simultaneously engage the regions of those individual ostia. Preferable to this mode, however, the region between the inferior vein ostia need not be ablated or engaged with an anchored ablation element. This is because it is believed that a complete "box" pattern of conduction block which would otherwise result may create one or more new reentrant arrhythmia wavelets through the atrial wall tissue surrounding that box. Instead, it is believed preferable in many cases to create lesions which bridge these inferior ostia to the anatomical barrier of the mitral valve annulus.

Thus, stylet (5) or a proximal guidewire tracking member as previously described may be used to position a proximal end of an ablation element, such as second ablation element

(50) shown in FIG. 3, in the vicinity of the mitral valve annulus. In the case of a proximal guidewire tracking member in this application, a guidewire engaged with that member is placed anterograde from the atrium and into the ventricle through the mitral valve. The proximal guidewire tracking member is then advanced over the wire until positioned at the desired location along the mitral valve annulus. In either the stylet or guidewire tracking member variation, a long linear lesion may be thus formed between the anatomical structure of the superior or inferior vein ostia and the mitral valve annulus.

Figure 4:
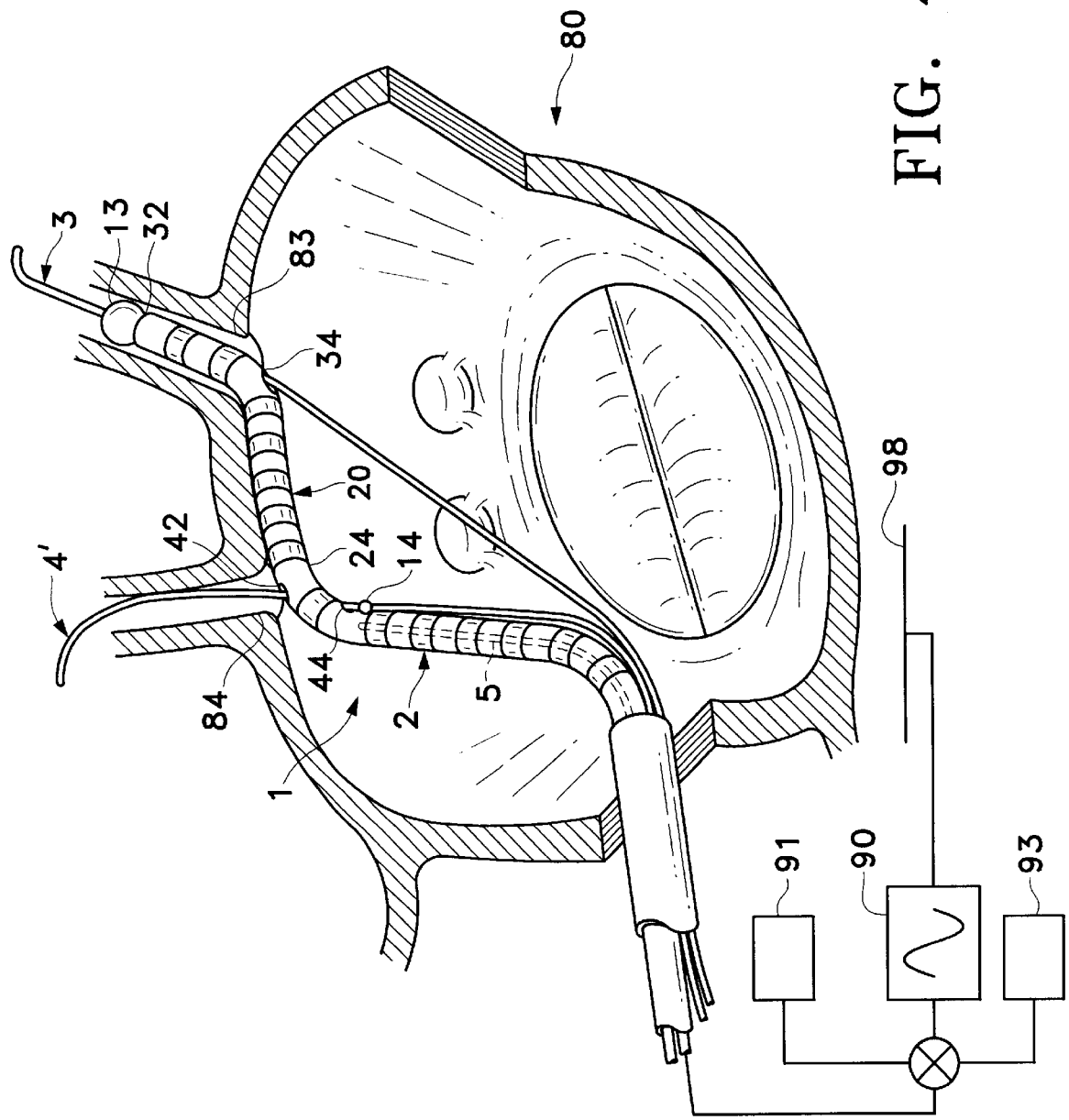
FIG. 4 shows a similar perspective view of the atrial lesioning device assembly shown in FIG. 3, although showing a further variation of the intermediate guidewire tracking member that anchors the proximal end of the ablation element adjacent the right superior pulmonary vein ostium.

FIG. 4 shows a further variation of the use of stop members on the engaged guidewires through the distal and intermediate guidewire tracking members of the current invention. In this variation, guidewire (4') includes a stop (14) which is positioned proximally of the second intermediate guidewire port (44). In this arrangement, the wire distal end portion is preferably "front-loaded" into the intermediate guidewire tracking member prior to introducing the wire into the body. This is because only such front-loading would result in the arrangement shown ("back-loading" of the guidewire would not be possible because the stop would block the tracking member from being positioned distally thereover). In this arrangement, guidewire (4') may be used to push the proximal end (24) of the ablation element (20) distally against the engaged pulmonary vein ostia in order to more firmly anchor the proximal end (24) into that ostium.

In addition to preferred shaped distal tips for the guidewires suitable in this variation, a guidewire region which includes or is located proximal of the stop may also have a shape in order to enhance this "pushing" function of the proximal stop variation. For example, a sweeping or discrete bend in the wire proximally of the stop may enhance directing the vector of force along the wire's length transversely from the wire's entrance into the left atrium through the guiding catheter in the fossa ovalis and toward the posterior atrial wall in the region of the pulmonary vein ostia.

Figure 5:
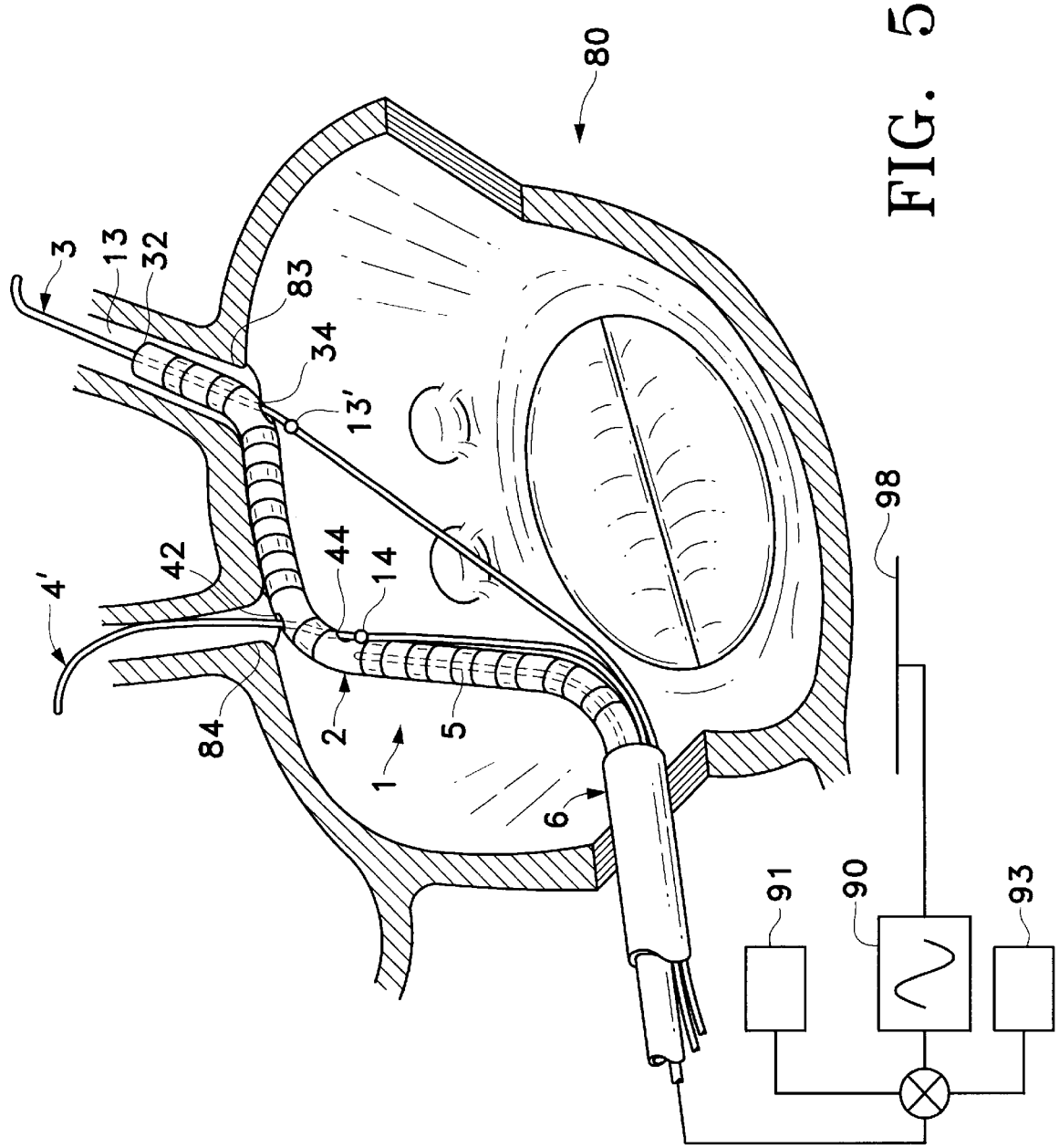
FIG. 5 shows a similar perspective view of the atrial lesioning device assembly shown in FIG. 3, although showing another variation for the distal guidewire tracking member that anchors the distal end of the ablation element adjacent the left superior pulmonary vein ostium.

FIG. 5 shows still a further variation incorporating the use of stop members on the guidewires to provide a means for forcing the engaged region of the ablation catheter against the tissue adjacent the vein ostia. In this variation, both guidewires (3,4') have stop members (13',14), respectively, which are positioned proximally of the respectively engaged distal and intermediate guidewire tracking members (30,40). According to the prior description by reference to FIG. 4, this assembly must be entirely "pre-loaded" with the distal ends of the guidewires inserted into the respective lumens of the respective tracking members. The assembly of this variation benefits from the ability to have force applied distally toward the desired anchoring locations in the adjacent pulmonary vein ostia via the proximally positioned stops on the guidewires.

Figure 6:
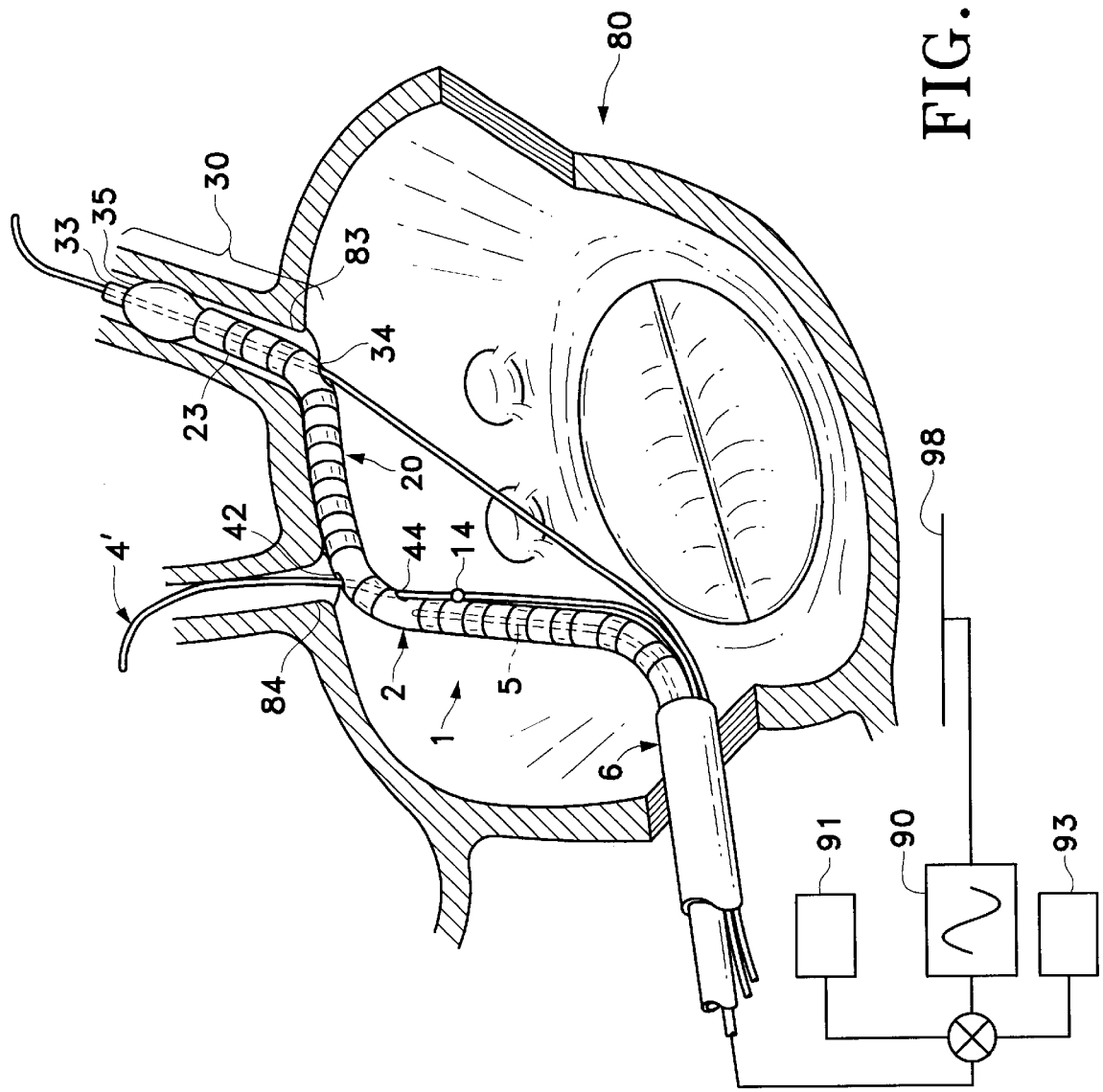
FIG. 6 shows a similar perspective view of the atrial lesioning device assembly shown in FIG. 3, although showing yet another anchoring variation at the distal end of the ablation element adjacent the left superior pulmonary vein ostium.

FIG. 6 show still a further variation of the ablation element anchoring feature of the current invention, wherein the distal end (23) of ablation element (20) is bordered by an expandable element (35) which is adapted to radially engage at least two opposite portions of the pulmonary vein wall within which the expandable element is positioned.

In this variation, the guidewire tracking methods for positioning the various regions of the ablation catheter relative to the pulmonary vein ostia may be substantially the same as for the previously described "guidewire stop" variations. However, once positioned, the device may be more substantially secured in that position due to the radial expansion of the expandable element.

In one mode, expandable element (35) is an inflatable balloon which is hydraulically coupled to a pressurizeable fluid source. Upon pressurization of the fluid source, fluid is forced into the balloon to hydraulically expand its diameter at least until circumferentially engaging a portion of the vein wall. In this mode, regions of the ablation catheter proximal to the balloon must provide a hydraulic fluid conduit such as an isolated inflation lumen that is coupled both to the balloon and also to the pressurizeable inflation source through the proximal coupler, as would be apparent to one of ordinary skill. Preferably, the inflation source includes a source of radiopaque fluid which is adapted for visualizing inflation characteristics of the balloon upon Xray fluoroscopy.

One suitable mode of construction for expandable element (35) as an inflatable balloon is as follows. The balloon may be a relatively elastic, expandable tubing, such as a latex rubber or silicone tubing, or may be a relatively less compliant, folded balloon, such as a polyethylene, polyolefin copolymer, polyvinyl chloride, or nylon balloon, which has relatively slight, controlled compliance during pressurization. In the case of an elastically constructed balloon, the balloon may have predetermined sizing based substantially upon volume of fluid used to inflate the balloon. In the less compliant construction, a kit of ablation catheters with several predetermined sizes over a range of operating pressures may be provided in order to accommodate varying pulmonary vein anatomies and diameters.

In other modes of this variation, expandable element (35) may be radially expandable in ways other than hydraulic inflation of a balloon. For example, a radially expandable cage may provide enough radial force on the vein wall to provide a sufficient anchor to that region of the ablation assembly. Other expandable members may also be suitable, such as those described in U.S. Pat. No. 5,509,900 to Kirkman, which is herein incorporated in its entirety by reference thereto.

Further to the modes described and obvious variations thereof, expandable element (35) may also be adapted to preferentially expand in one radial direction versus another, such that the central axis of the underlying elongate body is biased to one side of the expanded element's diameter. This may for example be particularly desirable for forcing the most distal electrodes of the ablation element, which are adjacent the expandable element, against a particular portion of the pulmonary vein wall. Without such radial bias, it is believed that a lack of intimal wall contact may result in regions of the elongate body adjacent to the expandable element. Preferably, the bias forces the adjacent region of the ablation element against the interior wall of the vessel which is between the anchors, thereby resulting in a long continuous lesion that extends with continuity up into the engaged vein.

Figure 7:
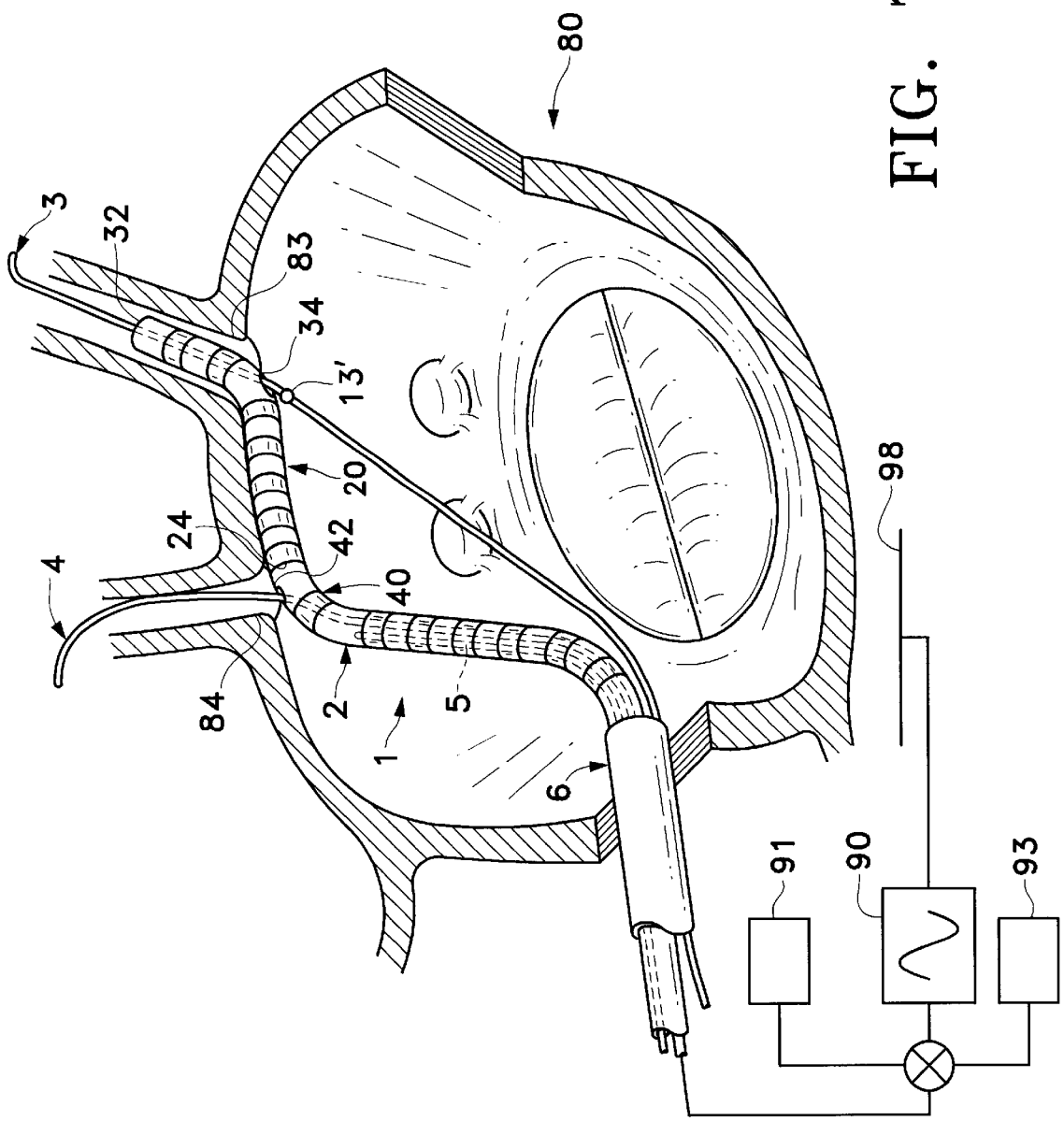
FIG. 7 shows a similar perspective view of the atrial lesioning device assembly shown in FIG. 5, although showing a further variation for the intermediate guidewire tracking member that anchors the proximal end of the ablation element at the right superior pulmonary vein ostium.

FIG. 7 shows a further variation of the intermediate guidewire tracking member (40) which forms the anchor adjacent the proximal end (24) of the ablation element (20). In contrast to the previously described variations, the intermediate guidewire tracking member (40) includes an intermediate lumen which has a second intermediate guidewire port (not shown) which is located at or near the proximal end portions of the ablation catheter (2), such as at the proximal coupler (not shown). It is believed that this elongated coaxial arrangement of at least one of the guidewire tracking members may provide a benefit in reducing the number of devices which are exposed to the internal bores of the delivery device and also within the atrium. Similarly, the need to include means for the intermediate guidewire to traverse the diameter of the elongate body as described by reference to FIGS. 2A–E above is removed by this variation.

Figure 8:
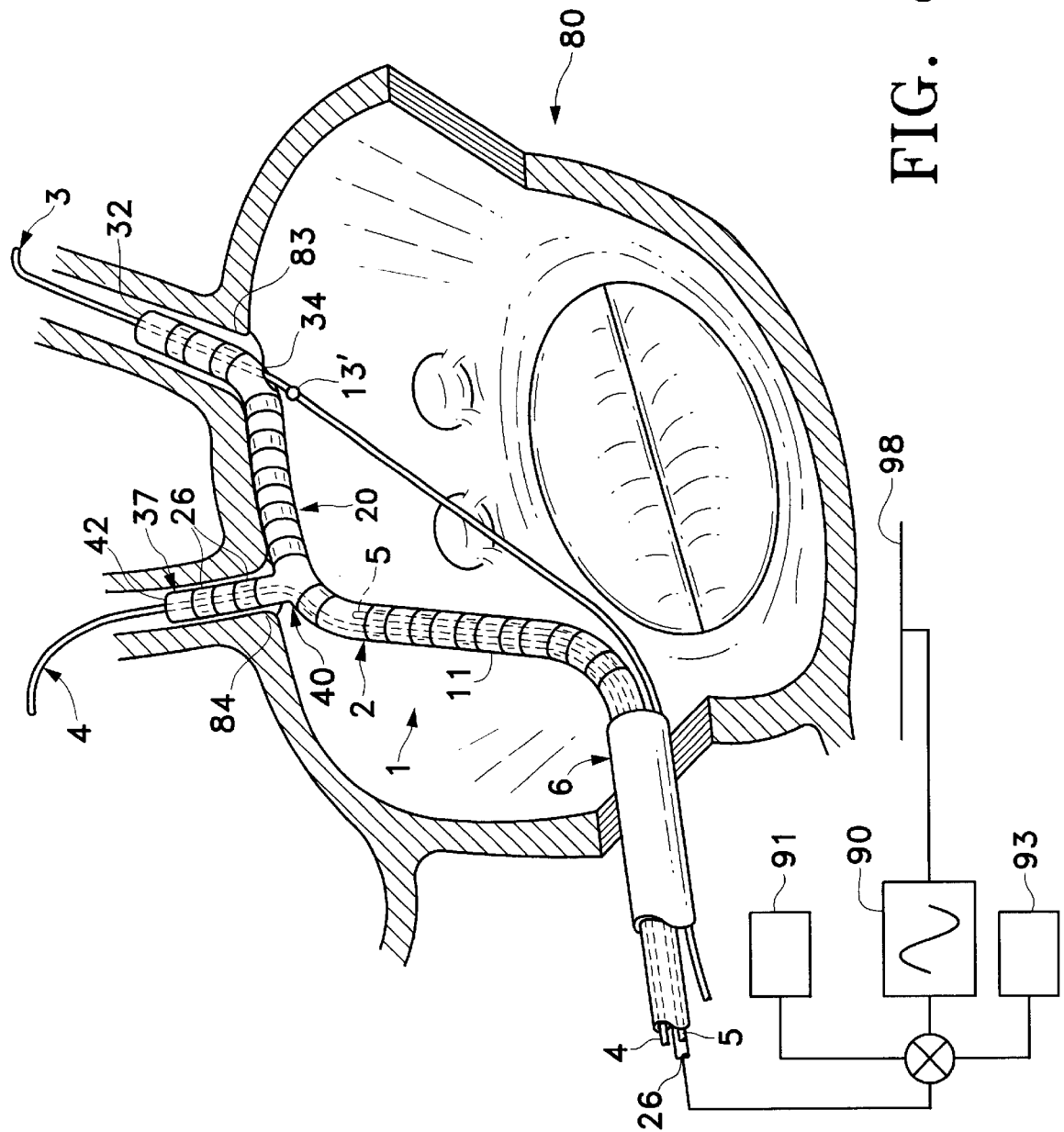
FIG. 8 shows a similar perspective view of the atrial lesioning device assembly shown in FIG. 7, although showing yet a further variation for the intermediate guidewire tracking member that anchors the proximal end of the ablation element at the right superior pulmonary vein ostium.

Building upon the variation shown and described with reference to FIG. 7, FIG. 8 shows the distal end portion of ablation catheter (2) to be branched such that intermediate guidewire tracking member (40) includes an intermediate leg (37). In this variation, the intermediate leg (37) provides a platform upon which additional electrodes (26) may be positioned to allow the proximal end of ablation element (20) to extend further into the second pulmonary vein ostium in which the intermediate guidewire tracking member (40) is anchored.

Intermediate leg (37) may be constructed according to a variety of methods. In one method, a first polymeric tubing includes proximal shaft (11) and has a port formed through its outer wall and into a lumen formed by that tubing. A second tubing of similar material is placed snugly over a mandrel, such as a teflon coated stainless steel mandrel, which mandrel is inserted into the lumen through the port until the end of the second tubing circumferentially engages the port. Preferably in this method the port and the engaging end of the second tubing (which is actually a second port) are adapted with predetermined geometries sufficient to mate their orifices to form a substantial seal at their interface. The engaged region of tubings is next placed next to an inductive heating source which is energized to sufficiently heat the adjacent region of mandrel in order to melt the region of the second tubing and thereby splice the tubings together in that region.

After heating as described, the mandrel is removed. In addition to the two-tubing adaptation just described, an additional step may be to heatshrink a third piece of tubing over the two-tubing adaptation prior to removal of the mandrel in order to provide some additional structural integrity to the adaption. In this method, the second tubing may be either the intermediate leg (37) or the distal end portion of the ablation catheter (2).

An additional method of forming the branched intermediate and distal end portions of the ablation catheter of the current invention may be as follows. An extruded polymeric tubing having two round lumens separated by a central wall, or a "dual lumen" extrusion, is cut to a predetermined length. One end of the dual lumen extrusion is cut along the tubing's longitudinal axis through the central wall to create the bifurcation. The resulting branched tubings in this alternative method may then be "post-processed" to prepare the tubings for adapting the electrode elements along their length, as would be apparent to one of ordinary skill. For example, the flat surfaces created by the formation of the branched tubings just described may be rounded such as by grinding or by melting the tubing within pieces of coaxial heat shrink tubing while mandrels are placed within the tubings (the heat shrink tubing of this variation would be removed after heat shrinking, and would be a dissimilar material such as a teflon heat shrink tubing or a polyimide heatshrink tubing).

In a further alternative, the resulting flat surfaces of the branched tubings may be desired, particularly since these surface would be naturally oriented to confront the tissue within and between the pulmonary vein ostia. The ablation element such as a plurality of electrode sub-elements may be placed only onto the flat surfaces created and would thus be substantially isolated to the elongate region of tissue contact along the length of the ablation element.

Figure 9A:
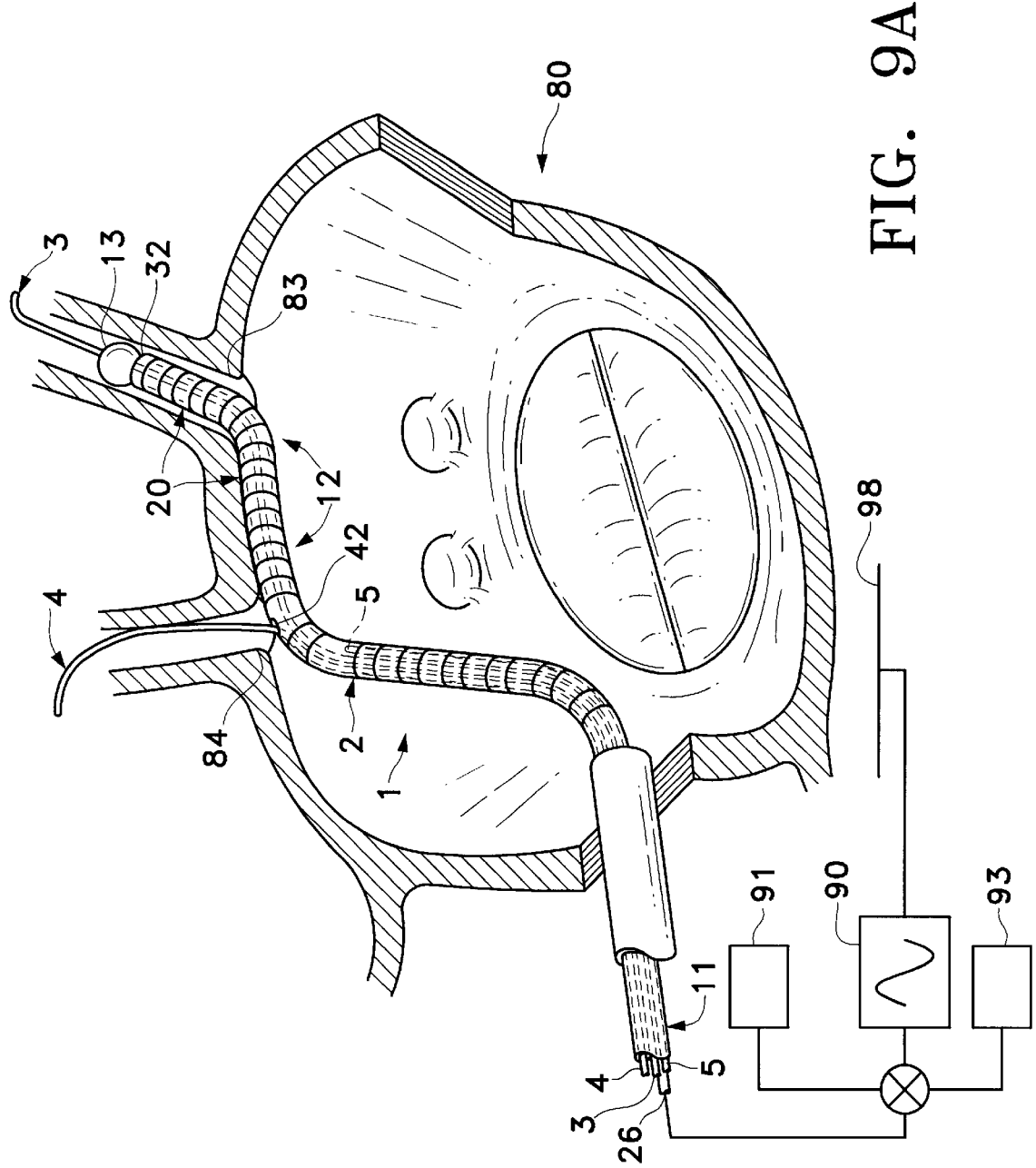
FIG. 9A shows a similar perspective view of the atrial lesioning device assembly shown in FIG. 7, although showing yet a further variation for the distal guidewire tracking member that anchors the distal end of the ablation element at the left superior pulmonary vein ostium.
Figure 9B:
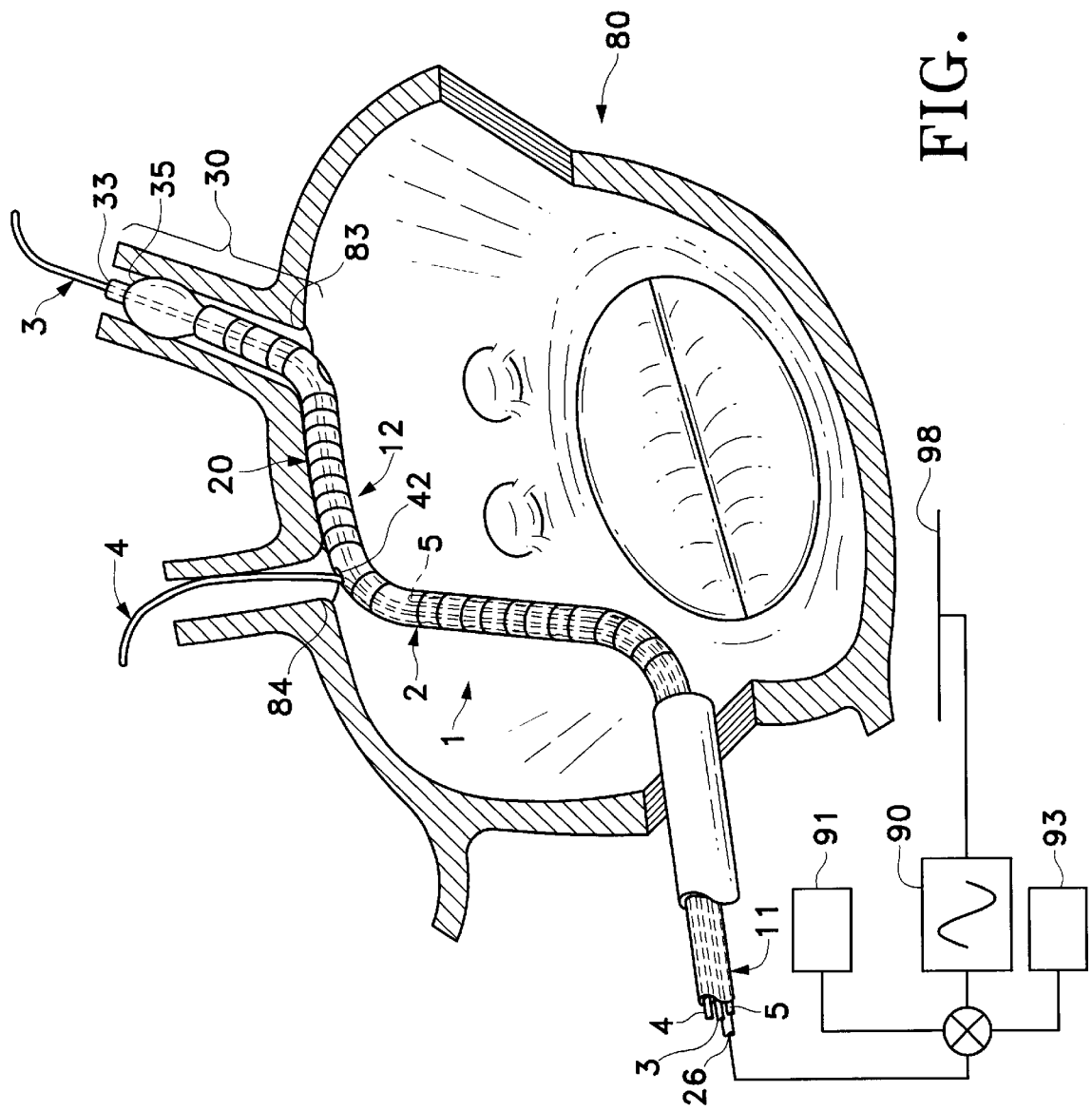
FIGS. 9B–C shows a similar perspective view as that shown in FIG. 9A, although showing yet a further anchoring variation at the distal end of the ablation element, shown in two modes of operation, respectively.
Figure 9C:
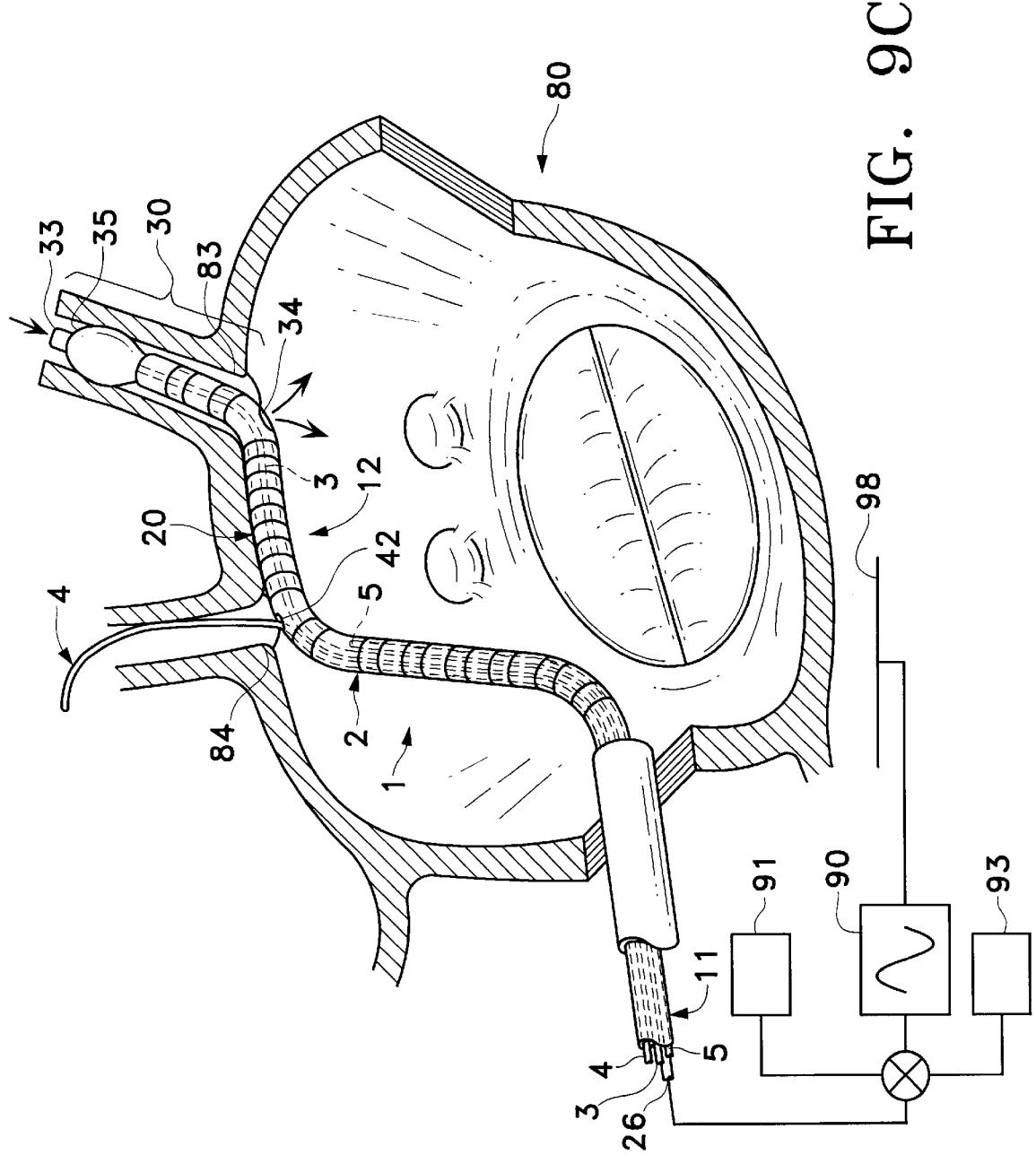

FIGS. 9A–C collectively portray a further variation of the distal guidewire tracking member as an anchoring means, which is shown in combination with the intermediate guidewire tracking member variation shown initially in FIG. 7. In this variation, neither of the guidewire tracking members has a second guidewire port located proximally of the first relative guidewire port in the region of the distal end portion of the ablation catheter. Rather, each of the distal and intermediate lumens extends proximally along the length of the elongate body of the catheter and terminates in a port (not shown) on the proximal end portion (11) of the catheter. Further to this variation, a stop may be provided on the guidewire engaged within the distal lumen of the distal guidewire tracking member, such as shown at stop (13') on guidewire (3) in FIG. 9A.

FIGS. 9B–C however show a different anchoring embodiment in the distal anchor than that shown in FIG. 9A. Rather than the use of a stop member on the guidewire (which could also be combined with the FIGS. 9B–C variation), the FIGS. 9B–C variation combines the catheter-guidewire tracking design of FIG. 9A with an expandable member anchoring mechanism at the distal device end, such as that shown previously in FIG. 6. Still different from the FIG. 6 variation for expandable element (35), the variation of FIGS. 9B–C allows for the guidewire (3) to be withdrawn proximally from the portion of the guidewire lumen which extends between the first distal guidewire port (33) and the second distal guidewire port (34). Therefore, according to the mode of operation shown in FIG. 9C, when the guidewire (3) is so withdrawn during expansion of the expandable element, blood flow is allowed to perfuse proximally through the open region of guidewire lumen and into the atrium (shown in bolded arrows). Without the guidewire and port arrangement provided in this variation, the expanded balloon in the variation shown would otherwise functionally occludes such flow. Furthermore, while the variation of FIG. 6 could functionally be used in the same manner by withdrawing wire (3) from the engaged lumen, wire engagement would be lost and would be substantially unrecoverable according to that design when used in remote body spaces such as in percutaneous procedures in the atrial chambers.

The present invention has been heretofore shown and described by reference to particular variations of anchors at distal and intermediate catheter regions adjacent to two opposite ends of an ablation element, respectively. These anchoring variations are adapted to allow for substantial tissue contact between the ablation element ends for creating a continuous, long linear lesion. However, it is further contemplated that the region of the ablation element itself may be additionally adapted to increase tissue contact along its length between the anchors at adjacent pulmonary vein ostia.

For example, the ablation element may include at least one ablation element anchor along its length which is adapted to engage the tissue adjacent to the element. In one particular embodiment, the ablation element anchor may be a suctioning means which includes at least one port in fluid communication with a vacuum source via a suction/air lumen extending through the body of the ablation catheter. An example of this embodiment is shown in overview fashion in FIG. 1, wherein further more detailed examples are provided in FIGS. 10A–F.

FIGS. 10A–E show various levels of detail of a similar ablation catheter variation as that shown in FIG. 7 for purpose of illustration, and show a more detailed mode which includes a suctioning anchor means in the region of the ablation element (120). The ablation element (120) includes a portion of a fluid lumen (127) which communicates exteriorly of the catheter device in the region of the ablation element through a plurality of fluid ports (128). These ports are positioned such that they face the tissue adjacent to the ablation element when the distal and intermediate guidewire tracking members (130,140) are anchored in adjacent pulmonary vein ostia. Fluid lumen (127) is adapted to couple to a vacuum source via a proximal coupler (not shown), in order to provide a suction force at the fluid ports (128) during ablation such that the ablation element is firmly in tissue contact during the ablation. Further included in this variation and shown in shadow in FIG. 10A and in cross section in FIG. 10E is an internal seal (129).

Seal (129) is located internally of fluid lumen (127) and distally therein relative to the most distal of fluid ports (128). This seal (129) provides one means for allowing for fluid isolation between the suction lumen in the region of the ablation element and the guidewire tracking member and its corresponding lumen. Various methods may be used for creating the seal (129), such as for example delivering a bolus of high viscosity or quick curing adhesive to the desired interlumenal location for the seal, or for example, by melting a plug of material within that lumen, or a combination of these or other methods.

Other means may also be used for enhancing tissue contact along the length of the ablation element in the alternative or in addition to the suctioning means just described. For example, the region of the catheter containing the ablation element, particularly between the ablation element's ends, may also be preshaped in a manner such that the ablation element has a bias into the tissue between the predetermined locations at which the ablation element ends are anchored. This bias may be heat set into the polymeric tubing making up the elongate body in the region of the ablation element, or may otherwise be formed, such as for example by providing a pre-shaped reinforcing member at that region of the elongate body. Such a pre-shape may be provided, as a further example, by means of the stylet (5) shown variously throughout the figures. In this mode, the stylet is adapted to advance distally into the region of the ablation element an to impart a biased shape to that region.

Both the suctioning means described, as well as the preshaped bias means, are designed to take advantage of a natural orienting feature of an ablation catheter according to the anchoring mechanisms of the present invention. When the anchors used in a particular variation are guidewire tracking members adapted to anchor in adjacent vessel ostia, such as in the variations heretofore described, the two guidewire tracking members will generally tend to take a natural, predictable orientation along the engaged guidewire axis. The ablation element extending between those oriented anchors will also generally tend to orient in a predictable fashion when engaged to the tissue in order to accommodate the preshaped bias variation and the fluid port/suction variations just described for the ablation element of the current invention.

FIG. 10F shows a further variation of the device assembly shown in FIGS. 10A–E, wherein the ablation element (220) has been modified. An energy sink (270) is provided in this variation which, rather than being disposed in a fixed orientation on the external surface of the elongate body, is instead slideably engaged within a lumen (not shown) in communication with the plurality of fluid ports (228). The energy sink (270) may be any of the alternative energy sources or other ablation technologies introduced above, such as an RF electrode, microwave antenna, cryoablation probe, fiber optic laser source, or ultrasound source. Preferably, however, the ablation means of this variation is adapted to ablate through the ports as it is moved to traverse across those ports while actuated for ablation.

It is further contemplated that the plurality of ports shown in FIGS. 10A–E might be engaged to mechanical, tissue engaging tools via coupled lumens within the interior regions of the device. In one mode, each of a plurality of ports is slideably engaged to a needle which is adapted to advance through the port and into the adjacent tissue as an anchor.

Ablation Element

The particular geometry and dimensions of the electrodes along the length of the ablation element (20) may effect the overall ablation characteristics, and a variety of arrangements may be suited for particular applications without departing from the scope of the present invention. However, these electrodes generally may be made of electrically conducting material, such as copper alloy, platinum, or gold, and may be wrapped about the flexible body of the device. Furthermore, in order to effectuate efficient ablation the electrodes should generally be designed to provide a suitable contact area with the tissue wall adjacent to the ablation element when anchored in place.

Still further, where a plurality of spaced electrodes are used such as in the variation of FIG. 1, the length and spacing of the electrodes may be particularly adapted to accommodate the ablation energy to be used. This combination is desired in order to optimize the creation of a continuous, long linear pattern of ablation which includes the regions between the electrodes. For example, particularly in the case of creating long linear lesions in atrial wall tissue, it is believed that gaps in such lesions may provide a route for reentrant atrial arrhythmia which might otherwise be blocked with a suitably contiguous lesion. Furthermore, it is believed that the desired lesions should be transmural, or from one side of the atrial wall to the other, in order to effectively block aberrant reentrant signals from bridging across the lesion and resulting in arrhythmia.

One electrode construction which is believed to be particularly well suited for use in ablating long linear lesions in the left atrial wall is as follows. A plurality of electrodes is provided along the ablation element, each electrode being constructed of a circumferentially coiled metallic wire, preferably a platinum wire. Each coiled electrode has a width that preferably ranges from 5 to 8 millimeters, and each adjacent pair of electrodes is preferably spaced 1 to 2 centimeters apart. It is believed that simultaneously energizing a plurality of electrodes according to this construction at a frequency of 500 kHz and at a power level ranging from 50–100 W will form a long linear lesion in atrial wall tissue sufficient to form a conduction block in many cases. The number of electrodes positioned along the ablation element according to these parameters may vary depending upon the overall desired ablation element length in order to form a particular long linear lesion. An initial overview of one electrical coupling arrangement for the ablation element of the current invention was provided by reference to FIGS. 1 and 3–9C. Further to the variations of those figures, signal recording device (91) may be coupled to the electrodes of the ablation element for the purpose of monitoring for arrythmias prior to, during, or after ablation is performed with those same electrodes, as would be apparent to one of ordinary skill. This recording device is preferably used after anchoring the ablation element at the desired region for forming the desired long linear lesion. Such recording of atrial electrograms allows a treating physician to: (1) confirm arrhythmia in the region of anchored ablation element; (2) define the anatomical limits of the atrial tissue along the ablation element length (when monitored at each electrode, such as extending outwardly along the wall of the pulmonary veins); (3) to assess the closeness of the ablation element to the mitral valve annulus (both atrial and ventricular electrical signals appear at the respective leads when at the annulus); and (4) to monitor conduction block after performing an ablation. It is believed that, by adequately securing and anchoring the ablation element to the ablation region before, during, and after ablation, accurate recording and subsequent analysis of the treatment may be achieved in a beating heart.

In more detail, one example of a suitable recording device for use with the present invention is the "CardioLab"™ system by Pruka Engineering Incorporated ("PEI"), located in Houston, Tex.

Further to the understanding of pacing device (93) shown variously throughout the previous figures, that device selectively allows artificial stimulation to the region of ablation in order to assess the conduction block ideally formed. In one mode, the ablated tissue is preferably dead and non-conductive and actuating the electrodes along that region via a pacing rhythm should not result in significant atrial wall conduction or wall motion response. Furthermore, by shifting the ablation element off-axis of the ablation region, pacing may be achieved and conduction block of a known signal may be assessed. One example of a suitable pacing device for use with the present invention is the programmed pacing stimulator made by Bloom, Inc. In one exemplary mode of operation, 1–20 mA of current in a square wave with a pulse width of 1 to 10 msec may be sufficient to induce arrhythmias to monitor the region of conduction block, or to pace map, or to measure pacing threshold of the targeted tissue pre- or post-ablation.

For purposes of providing a more thorough understanding of the structure of the ablation element, itself, FIGS. 11–14 provide more detailed views of variations for the ablation element as it is positioned on the ablation catheter.

Figure 11:
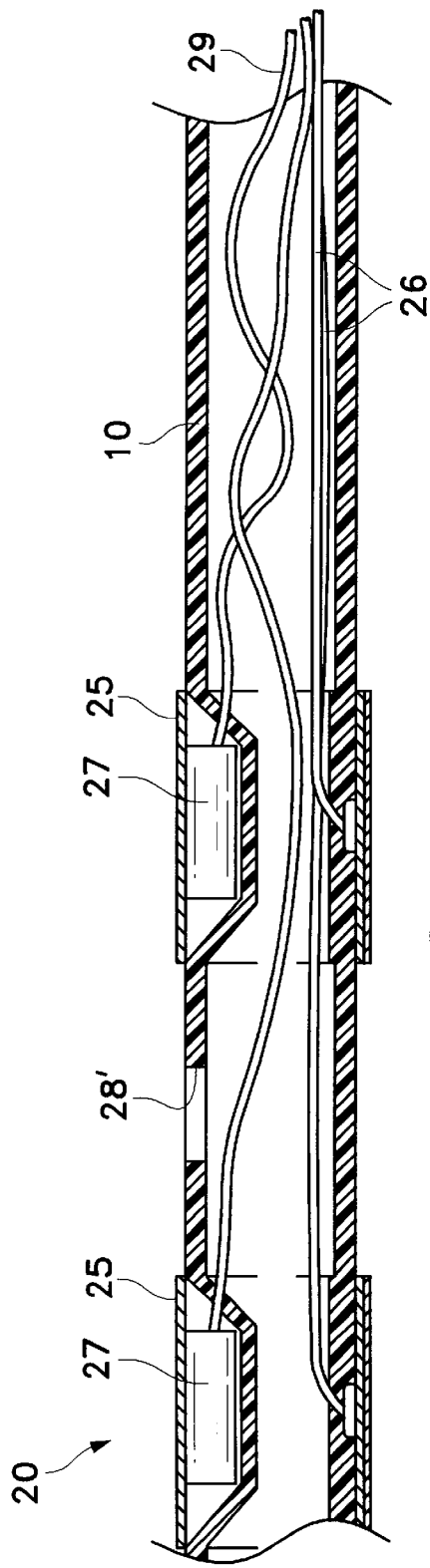
FIG. 11 shows a side sectional view of one ablation element variation for use in the ablation device assembly of the current invention and shows each of a plurality of thermistors positioned beneath an electrode for use in monitoring the temperature adjacent the electrode during ablation.
Figure 12:
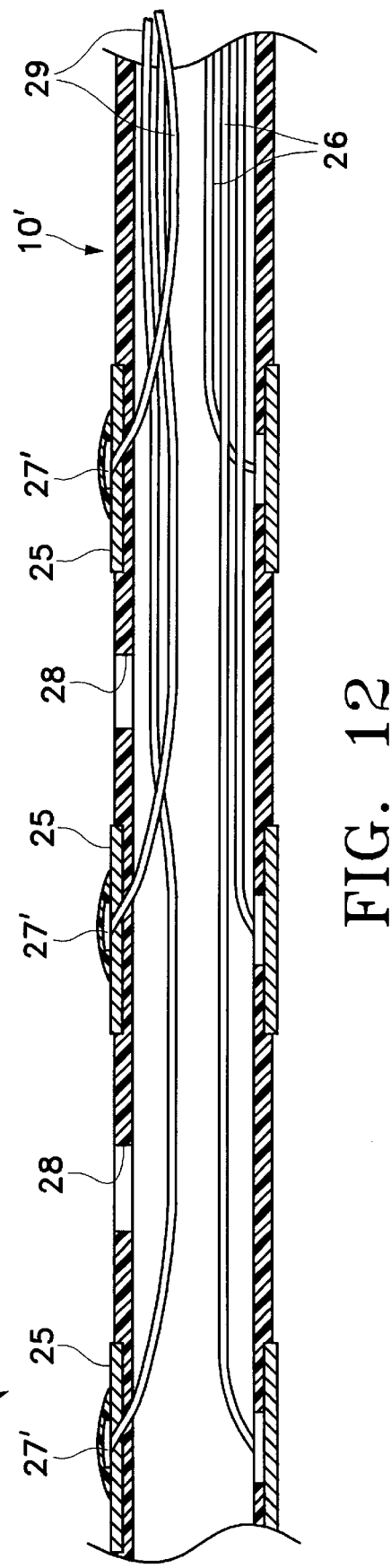
FIG. 12 shows a side sectional view of another ablation element variation for use in the ablation device assembly of the current invention and shows each of a plurality of thermocouples positioned beneath an electrode for use in monitoring the temperature adjacent the electrode during ablation.
Figure 13:
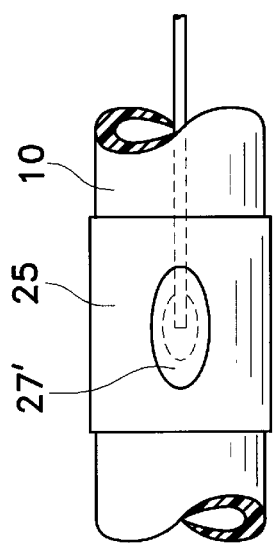
FIG. 13 shows an exploded perspective view of one thermocouple and electrode used in the ablation element shown in FIG. 12.

FIG. 11 shows a plurality of electrodes (25) which are coupled to electrode leads (26), respectively, which are shown to extend proximally along the length of the catheter elongate body (10) where they are then engaged to at least one electrical coupler (not shown).

Ablation element (20) may also include temperature monitoring elements, as are also shown in FIG. 11 at thermistors (27). The inclusion of these thermistors (which may also be thermocouples) provide a means for measuring the temperature in the region of the ablation element for purposes of feedback control during the ablation procedure. Each of thermistors (27) is shown in FIG. 11 to be positioned in the vicinity of one of the electrodes (25) and is also coupled to one of temperature monitoring leads (29). A further variant of the embodiment shown in FIG. 11 is provided in FIGS. 12 and 13, wherein thermocouples (27'), instead of thermistors, are shown in the vicinity of the electrodes (25). More detail regarding the particular size, material, dimensions, and methods of constructing the electrode and temperature monitoring elements onto a catheter as just described may be found by reference to U.S. Pat. No. 5,582,609 to Swanson et al., which has been previously incorporated by reference.

Figure 14:
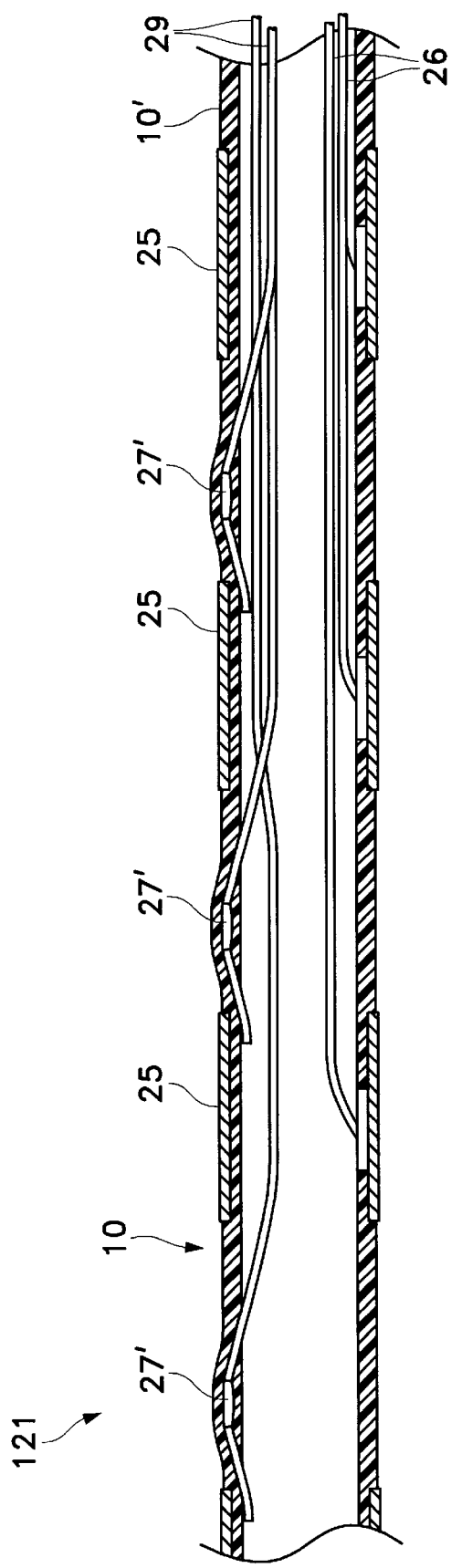
FIG. 14 shows a side sectional view of a similar ablation element variation for use in the ablation device assembly of the current invention as that shown in FIG. 12, although showing the plurality of thermocouples positioned between ablation electrodes.

Furthermore, the temperature monitoring elements may be either coupled directly to the electrodes, or may be otherwise positioned along the length of the ablation element as would be apparent to one of ordinary skill. For example, FIG. 14 shows such an alternative arrangement of thermocouples (27') between adjacent electrodes (25) along the ablation element (121).

The electrode and temperature monitoring designs just described merely represent specific embodiments for use with the broader present invention. Additional suitable ablation elements are described above in overview fashion by reference to prior known references, the disclosures of which have been incorporated by reference. In particular, however, more detailed examples of coiled electrodes coupled with temperature monitoring mechanisms for use in the current invention are described in U.S. Pat. No. 5,582,609 to Swanson et al., which has been previously incorporated by reference above.

Figure 15A:
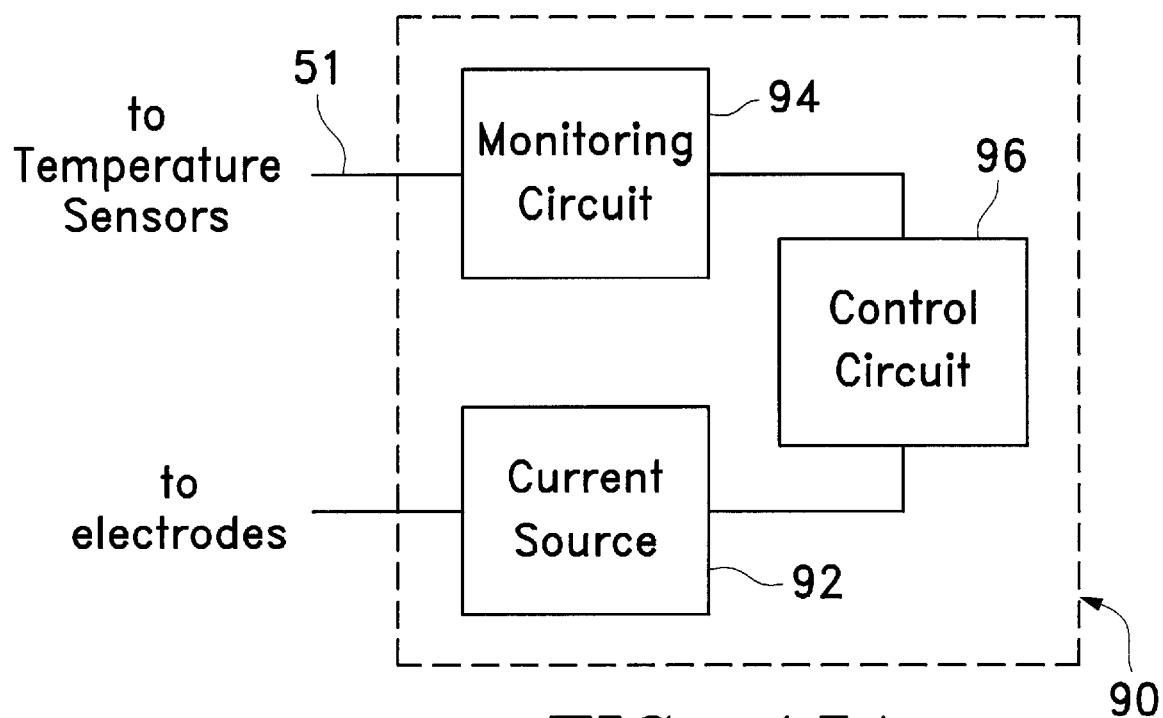
FIGS. 15A–B show schematical views of alternative feedback control variations for use in the ablation actuator of the ablation device assembly of the current invention.
Figure 15B:
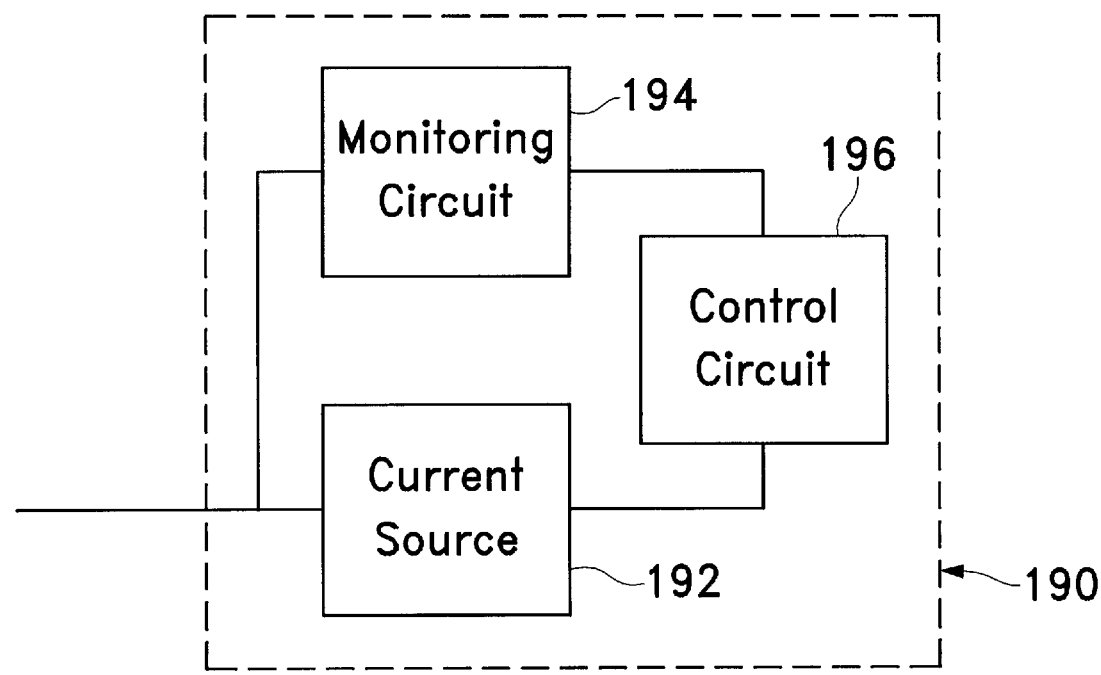

More detail regarding suitable examples for an ablation actuator for use with the ablation element embodiments herein described is provided by reference to the schematic depiction of ablation actuator (90) in FIG. 15A. Ablation actuator (90) in the FIG. 15A variation includes a current source (92) for supplying an RF current, a monitoring circuit (94), and a control circuit (96). The current source (92) is coupled to the ablation element (not shown) via the electrode leads in electrical coupler (51), and is also coupled to the ground patch (98). Monitoring circuit (94) is coupled to the thermistor leads in electrical coupler (51), and also to control circuit (96). Control circuit (96) is in turn coupled to both the monitoring circuit (94), and also to the current source (92) in order to adjust the output level of current driving the electrodes based upon the relationship between the monitored temperature and a predetermined temperature set-point.

The feedback control circuit just described is therefore based upon comparing the measured, real-time temperature of the ablation region against values known to indicate ablation progress. A monitored temperature may for example signal the completion of ablation and therefore trigger cessation of energy delivery. Or, such values may indicate the quality of tissue contact, which information may be used in the control circuit to adjust the drive current to the region at issue. Furthermore, a particular set-point may be predetermined based upon known empirical values, or may be patient dependent, as would be apparent to one of ordinary skill.

In addition to, or in the alternative to the temperature control feedback mechanism just described, it is further contemplated that the electrical parameters of the RF ablation drive circuit may be monitored in order to provide suitable feedback control. For example, output voltage, output current, output power, impedance, or reflected power, or change or time rate of change of these parameters may be monitored and used in one or a series of feedback control algorithms. The real-time value of such monitored parameters have been observed to characterize the progress of some ablation procedures, and have also been used in control circuits for real-time feedback control of ablation drive current.

Each individual electrode of the plurality of electrodes in the ablation element may also be individually controlled in a control system, such as in a multiplexed system. One example of a feedback control system which is believed to be suited for such feedback control of the ablation elements provided with the present invention is described in WO 96/00036 to Panescu et al. Further examples of feedback control systems which may be adapted for use in the present invention according to one of ordinary skill based upon this disclosure are provided in U.S. Pat. No. 5,496,312 to Klicek; U.S. Pat. No. 5,437,664 to Cohen et al.; and WO 93/20770 to Strul. The disclosures of the feedback control references just described are herein incorporated in their entirety by reference thereto.

Long Linear Lesion "Box" as Conduction Block FIGS. 16–21 show the device assembly of the current invention in various steps during the completion of an overall atrial fibrillation treatment procedure, wherein a box configuration of conduction block is created around the region of the pulmonary vein ostia. Throughout this particular subset of figures, an atrial lesioning catheter device assembly similar to that shown in FIG. 5 is shown, for purposes of illustration, in various positions within a sectioned left atrium during sequential lesion formation between various predetermined pairs of pulmonary vein ostia.

Figure 16:
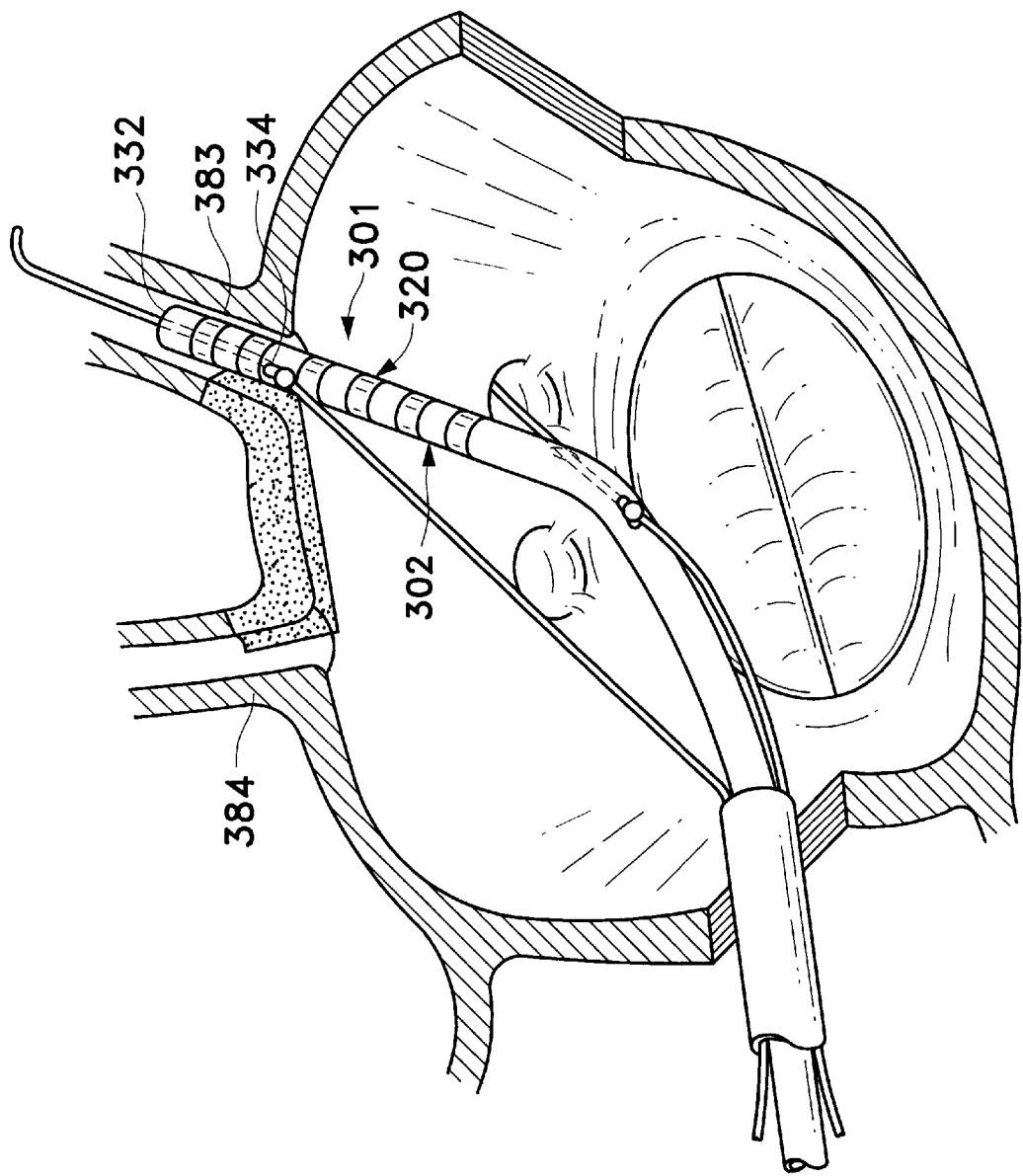
FIG. 16 provides a perspective view of the ablation device assembly shown in FIG. 5 during use in sequentially forming long linear lesions between the left superior and inferior pulmonary vein ostia.

FIG. 16 shows tissue ablation device assembly (301) after performing a first long linear lesion ablation procedure with the ablation element (320) of ablation catheter (302) positioned in a first position between the left and right superior pulmonary vein ostia (383,384) (first position not shown in this figure). In this figure, ablation catheter (302) is shown repositioned in a second position between the left superior and inferior pulmonary vein ostia for performing a long linear lesion ablation procedure between that pair of adjacent vein ostia.

Figure 17:
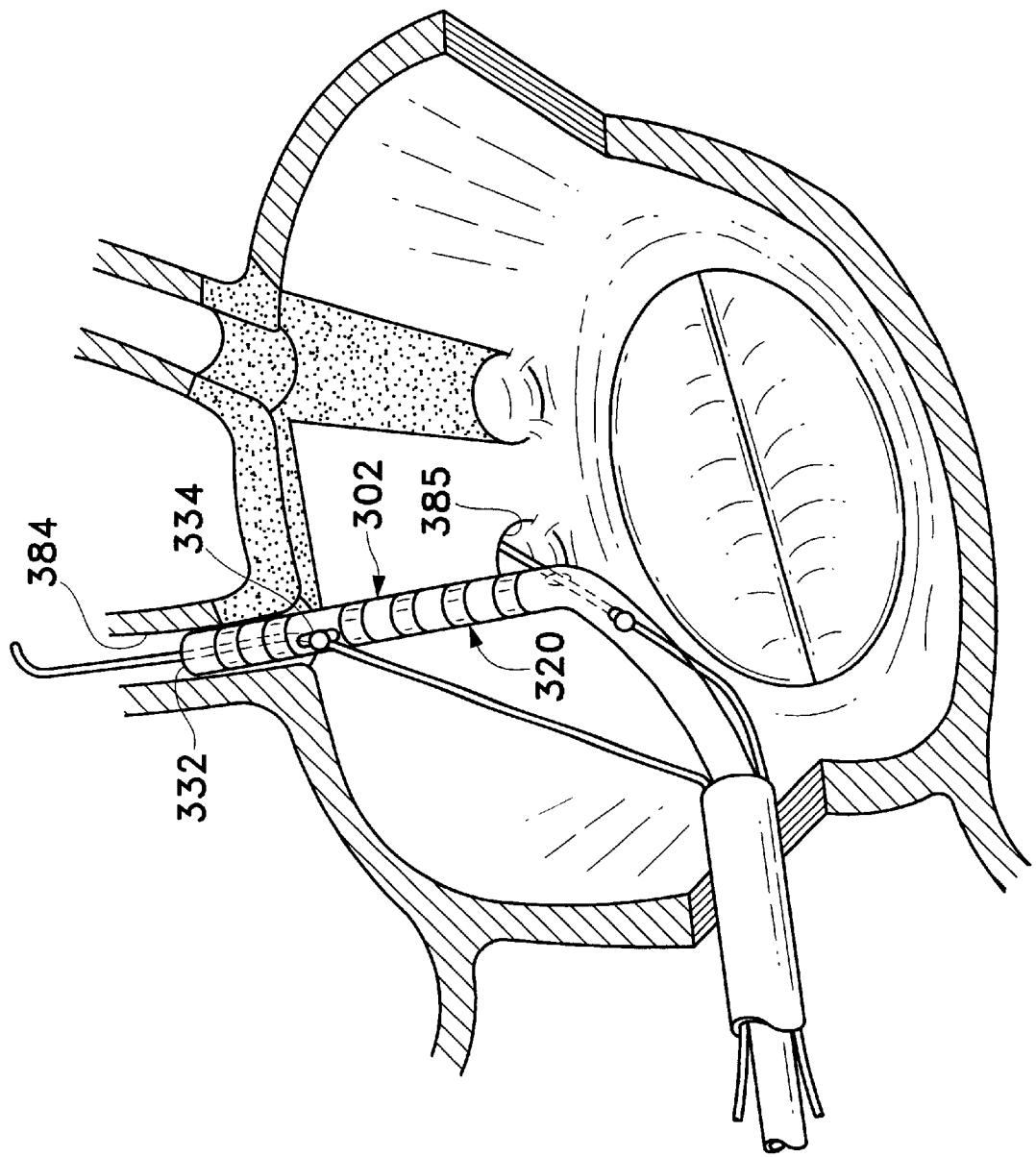
FIG. 17 provides a perspective view of the same ablation device assembly shown in FIG. 16, positioned in the right superior and inferior pulmonary vein ostia, shown after an initial formation of a long linear lesion between the left and right superior vein ostia according to the ablation element anchoring shown in FIG. 5.

FIG. 17 shows the ablation catheter (302) in the left atrium after performing a second long linear lesion ablation procedure according to FIG. 16, wherein the ablation element (320) is repositioned to a third position where its ends are anchored in the right superior and inferior vein ostia (384,385). Subsequent to performing this third linear ablation, an open ended box of lesions results between all adjacent pairs of vein ostia, but between the inferior vein ostia. This result may sufficiently treat some atrial reentrant fibrillation sequelae, as may any of the other interim results subsequent to each ablation lesioning step described for this procedure.

However, it is believed that many patients with multi-wavelet reentrant atrial fibrillation require complete isolation of the pulmonary vein ostia from the other atrial tissue. While one mode of achieving such complete isolation may be to connect the final leg of the conduction "box" between the inferior vein ostia, an alternative solution of forming a pair of lesions between these ostia and the mitral valve annulus at the base of the left atrium is also believed to be reasonable.

Figure 18:
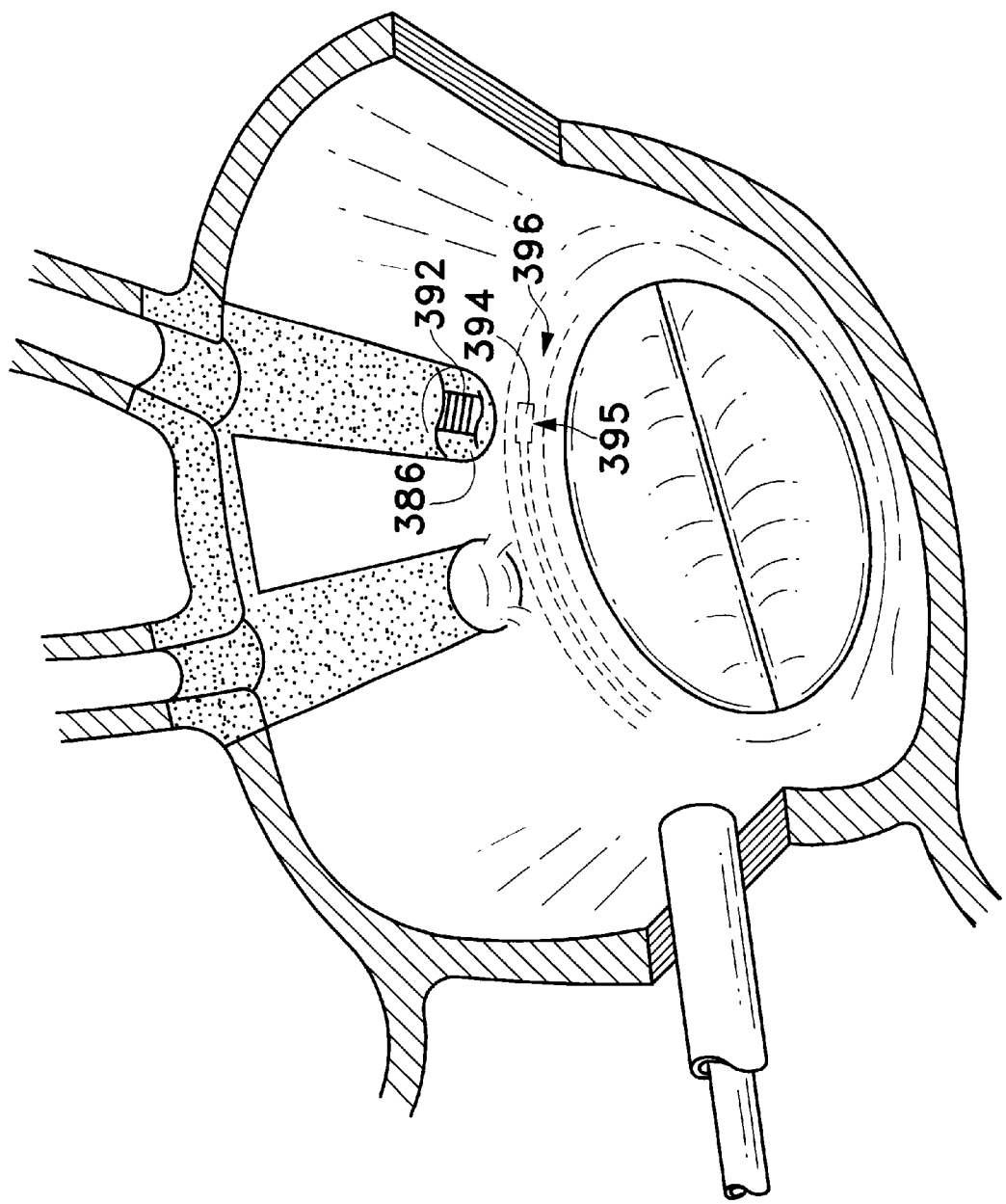
FIG. 18 shows a perspective view of a further atrial lesioning device assembly according to the current invention, showing the ablation element of a first ablation device positioned adjacent to a left inferior pulmonary vein ostia, and also showing in shadowed view the ablation element of a second electrode device positioned within the coronary sinus and adjacent to the first ablation element and the mitral valve annulus.
Figure 19:
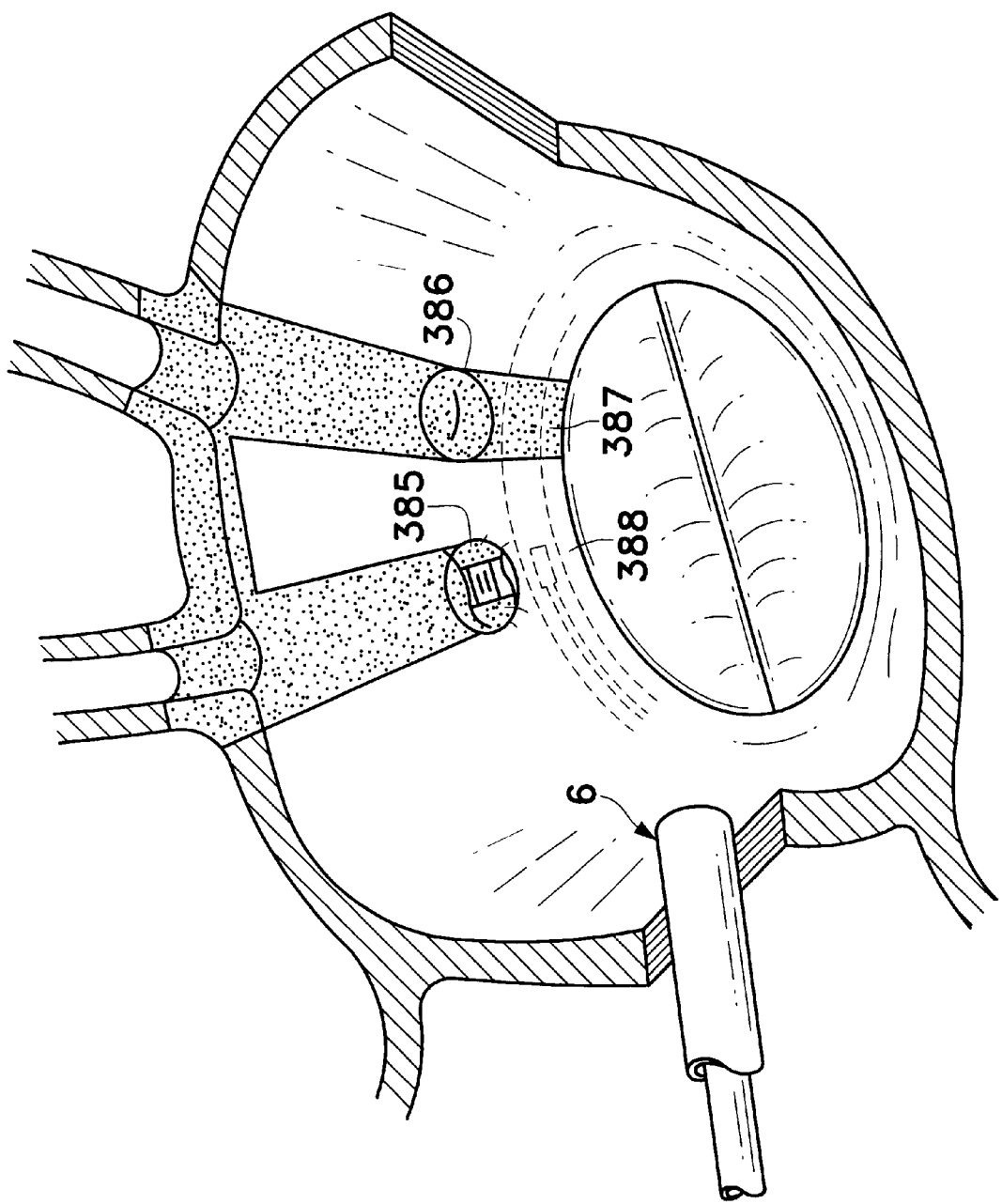
FIG. 19 shows a similar perspective view of the atrial lesioning device assembly shown in FIG. 18, although showing the ablation element of the first ablation device repositioned in the right inferior pulmonary vein ostium, and also showing the ablation element of the second ablation device repositioned along the coronary sinus adjacent to the first ablation element and the mitral valve annulus.

FIGS. 18 and 19 therefore show sequential steps in forming a pair of lesions between the inferior pulmonary vein ostia and the region of tissue adjacent to the mitral valve annulus. More particularly, FIGS. 18 and 19 provide a schematic representation of the intracardiac placement of two monopolar electrodes that are combined in a bipolar cardiac ablation arrangement which is adapted to form ablation lesions between the inferior pulmonary vein ostia and adjacent regions of the mitral valve annulus.

In FIG. 18, a first monopolar ablation electrode element (392) is shown positioned adjacent to the left inferior pulmonary vein ostia (386). As would be appreciated by one of ordinary skill, this electrode may take many suitable forms in this application regarding its incorporation onto various catheter platforms, and is therefore represented schematically. In one exemplary mode not shown, the electrode may be at least one of the electrodes along the length of an ablation element as provided in the previous variations of the invention. For example, the electrode may be at the end of an ablation element adjacent to the catheter's most distal end, such as the electrode shown between guidewire ports (332) and (334) in FIGS. 16 and 17. In this example, the electrode may be positioned within the inferior pulmonary vein ostium as would be apparent to one of ordinary skill according to the teachings of the variations above.

A second ablation electrode element (395) is also shown in shadowed view in FIG. 18 positioned within the coronary sinus (396) and is positioned along that lumen such that it is adjacent to the first electrode element (392). Again, this electrode may comprise one of several known electrode configurations and be sufficient for the purposes of this bipolar ablation step, hence the schematic representation in the Figure.

The second ablation electrode element (395) is positioned in the coronary sinus as follows. Initially, a guiding catheter is introduced into the right atrium either via the superior or the inferior vena cavae according to known methods (and according to some of the same methods described in more detail above). Next, the device is introduced through the guiding catheter and into the coronary sinus through its ostium in the right atrium, which may be accomplished by tracking the second electrode carrying device (394) over a steerable guidewire which has previously sub-selected the coronary sinus distally of the guiding catheter. Or, in the alternative, the guiding catheter or a second guiding catheter within the original guiding catheter may be shaped and otherwise adapted to engage the coronary sinus ostium along the right atrial wall and thereby provide a lumenal conduit into that vessel.

Once in the coronary sinus, the second electrode (394) may be positioned relative to the first electrode using a variety of techniques. In one variation, the electrical potential between the two electrodes may provide a measure of their relative distance from each other. This measure may provide a telling inflection point as the second electrode is advanced through the coronary sinus and across the position closest to the stationary, anchored first electrode. In another variation, the first and second electrodes are each sufficiently radiopaque such that their relative distance from each other is easy to visualize via Xray fluoroscopy.

Regardless of the particular makeup of the electrodes or mode of directing and fixing their relative positioning, once so positioned an electrical signal transmitting therebetween serves to ablate the atrial wall tissue therebetween, as would be apparent to one of ordinary skill.

FIG. 19 shows a similar schematic view of first and second electrode devices as that shown in FIG. 18, although showing the devices in a second position wherein they are collectively adapted to ablate a long linear lesion between the right pulmonary vein ostium (385) and an adjacent region of the mitral valve annulus (388). In this figure, a long linear lesion is shown between the left pulmonary vein ostium (386) and an adjacent region of the mitral valve annulus (387) subsequent to its formation according to the device positioning of FIG. 18. As will be appreciated by one of ordinary skill, the lesioned "box" is thus completed by forming long linear lesions between and connecting the inferior pulmonary veins with the region of the mitral valve annulus.

Figure 20:
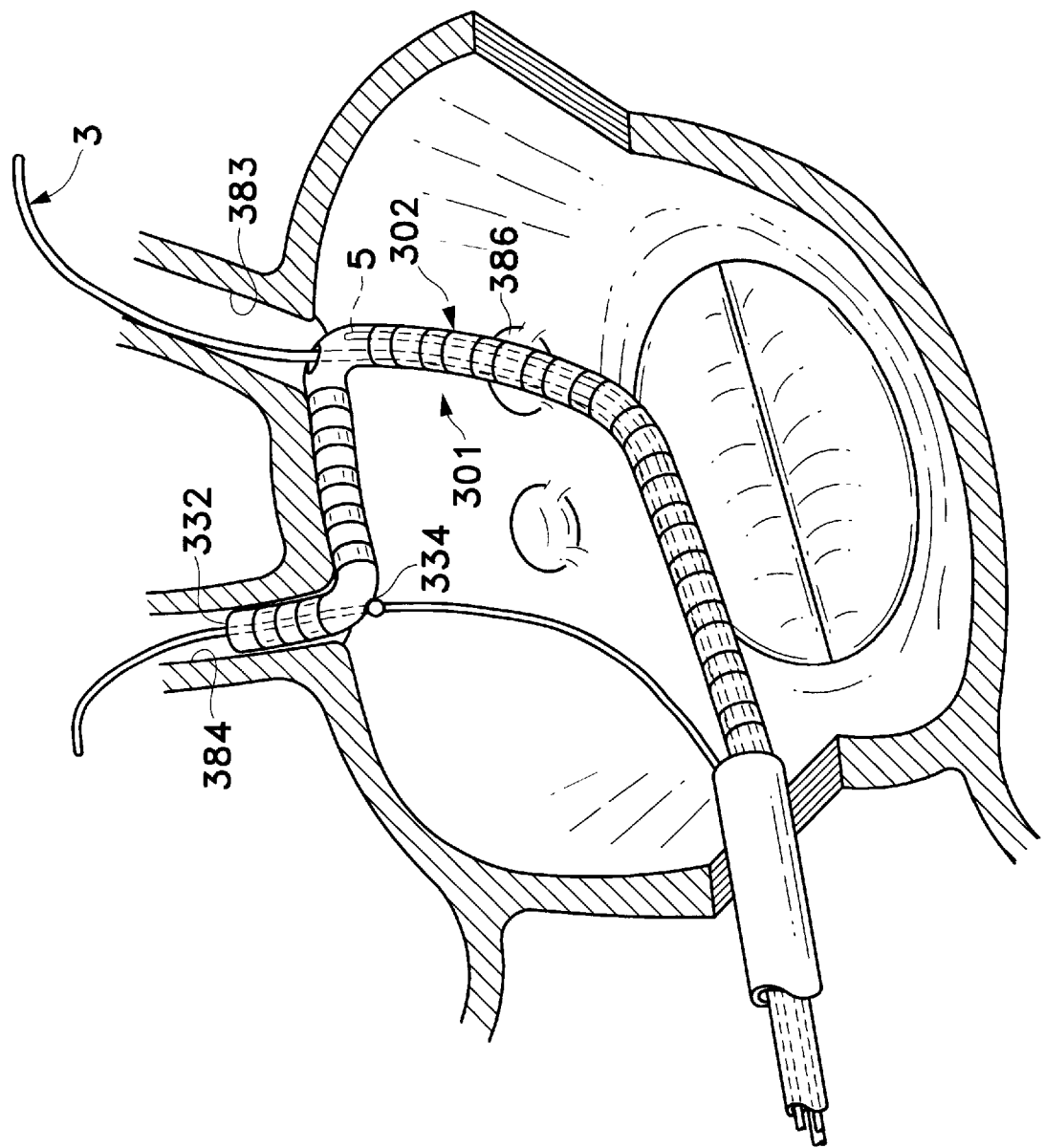
FIG. 20 shows a further embodiment of the ablation device assembly used in forming multiple long linear lesions during a single positioning event, wherein a stylet is shown during use to bridge the left superior and inferior vein ostia in addition to engaging the left mitral valve annulus for the purposes of creating a continuous long linear lesion.

FIG. 20 shows further a device assembly of the current invention in a single positioning event during an atrial fibrillation treatment procedure, wherein at least a portion of a conduction block is created around the pulmonary vein ostia and the mitral valve annulus in an assembly shown in a similar, reciprocal image as that view shown in FIG. 7. In this Figure, however, tissue ablation device assembly (301) is used to create multiple long linear lesions with various adjacently positioned ablation elements along its body and. In one aspect of this assembly, an ablation element (320) has each of two ends anchored in the two adjacent superior vein ostia (383,384). In a further aspect, a second ablation element (325) is provided proximally of the anchor engaged to left superior ostium (383) and is anchored distally by that same anchor and more proximally is positioned against the wall via a shaped stylet (305). Further to this aspect, shaped stylet (305) is adapted to impart a shape to the catheter shaft in the region of the second ablation element such that the shaped region of the ablation element substantially conforms to the tissue of the adjacent atrial wall. Still further, stylet (305) adapts the region of the second ablation element to traverse the left inferior pulmonary vein ostia (386) to the region of the coronary sinus so as to engage the mitral valve annulus. In this manner, a single continuous long linear lesion is created.

In a further inferior vein ostium-mitral valve annulus lesioning variation not shown, it is further contemplated that a guidewire may be advanced antegrade from the left atrium and through the mitral valve into the left ventricle. In this manner, a rail is provided into the region of the mitral valve such that a correspondingly engaged guidewire tracking member on the tissue ablation catheter assembly according to the invention may be placed through the valve to anchor the ablation element against the mitral valve annulus.

Still further, in a retrograde arterial access approach to introducing the devices herein described into the left atrium, a guiding catheter tip is advanced into the left atrium through the mitral valve. It is also contemplated that that guiding catheter tip region may provide an additional ablation element to assist in completing the inferior leg of the barrier-to-barrier conduction block described by ablating a region between the inferior vein ostia and the mitral valve annulus.

Figure 21:
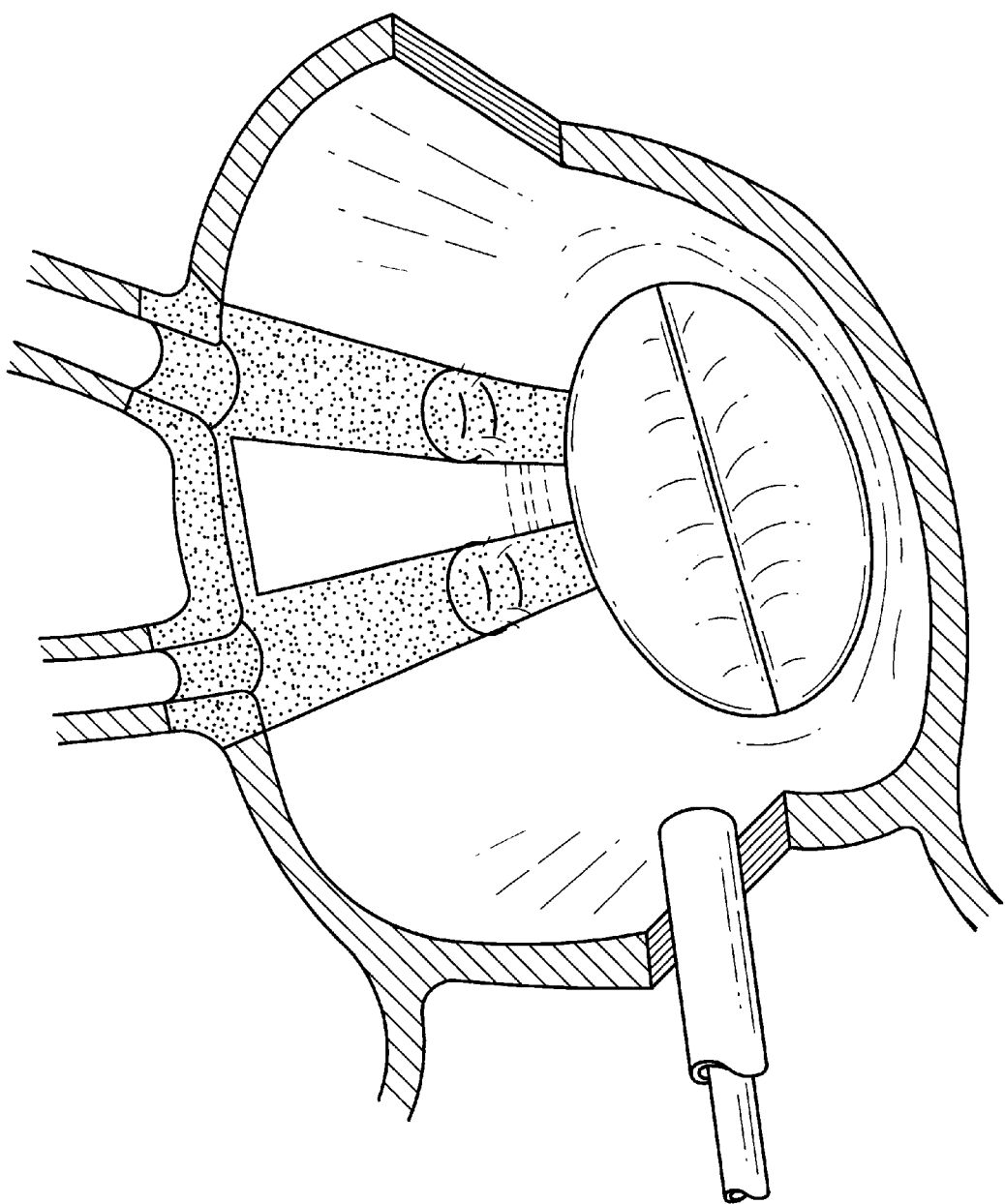
FIG. 21 shows a perspective view of the inner surface of an atrial wall subsequent to the multiple long linear lesion ablations performed according to FIGS. 16–19, or in part according to the multiple long linear lesions created by the variation shown in FIG. 20.

Regardless of the specific variation applied, the purpose of further illustration, FIG. 21 shows a completed "box" of long linear lesions formed according to the ablation catheter variations shown and described above, and particularly by reference to the sequential long linear lesioning methods shown and described with reference to FIGS. 16–19.

Further to the overall procedure of using the device assembly of the current invention, the initial placement of the ablation catheter assembly into the left atrium may be achieved using known access procedures according to one of ordinary skill. Generally, these procedures access the left atrium either transeptally from the right atrium through the fossa ovalis in the intra-atrial septal wall, or retrogradedly from the left ventricle and through the mitral valve (as introduced briefly above). The embodiments shown herein in the figures and described above have portrayed use of the present invention through a transeptal sheath approach for the purpose of consistent illustration. However, the device variations described are considered to be adapted or easily modified according to one of ordinary skill for use in the retrograde arterial approach from the ventricle into the left atrium. Nevertheless, a brief overview of one transeptal left atrial access procedure through the fossa ovalis is herein described for the purpose of providing a thorough understanding of an acceptable access method.

Initially, the right atrium is accessed with a guiding catheter or sheath through either the inferior or superior vena cava, which initially requires cannulation with an introducer sheath such as through the well known "Seldinger" technique.

Suitable guiding catheters for use in this procedure are also well known, but generally range from 7 to 12 French, preferably 8 to 120 French, and include shaped, radiopaque tips and torqueability for the purpose of steering and directing the catheter to the desired remote in vivo locations under Xray fluoroscopy. Importantly, at least one large lumen is provided in the guiding catheter for the purpose of providing a tubular conduit for the delivery of various object devices for treatment once properly located. Generally, a guidewire such as a 0.032" diameter guidewire is also provided coaxially within the guiding catheter lumen in a telescoping arrangement, also for aiding the directing the guiding catheter to the target site.

Once in the right atrium, the guiding catheter is directed toward the fossa ovalis, and is advanced through that septal opening to finally cannulate the left atrium and provide lumenal access into that body space to direct object treatment or diagnostic devices thereto. The access through the fossa ovalis may be achieved by advancing a "Brockenbrough" needle or trocar through a dilator, which assembly is against the fossa ovalis through the guiding catheter. The needle, dilator, and guiding catheter are then advanced through the fossa ovalis, after which the needle and dilator are withdrawn to leave the guiding catheter in place.

It is further contemplated that various diagnostic and other patient management regimes may be required ancillary to creating long linear lesions for treating left atrial fibrillation according to the current invention. For example, it is contemplated that several diagnostic procedures may be necessary prior to successfully performing the long linear lesioning treatments just described.

For example, patients are known to differ in their anatomical make-up in the region of the pulmonary vein Ostia. More particularly, Jafs et al. in a scientific abstract entitled, "Biatrial Dimensions Relevant to Catheter Ablation", North American Society of Pacing and Electrophysiology, 17th Annual Scientific Sessions Abstract Form, has previously disclosed finite ranges of distances between the various pairs of adjacent pulmonary vein ostia among human left atria. Based upon that disclosure, the range of distances between the superior pulmonary vein ostia is believed to be 31 to 55 millimeters (mean of 43+/−8 millimeters); and the range of distances between the superior and inferior pulmonary vein ostia is 25 to 46 millimeters (mean of 38+/−7 millimeters).

According to these ranges, providing only one length of ablation element according to the present invention may negate a sizeable, otherwise treatable patient population. It is contemplated that a kit of ablation catheter device assemblies may be required which includes various lengths of ablation elements between anchors. For example, providing a kit with available ablation elements having lengths ranging from approximately 15 millimeters to approximately 70 millimeters, and preferably ranging from approximately 25 millimeters to approximately 55 millimeters, may provide a suitable range to choose from in order to treat most patients. Furthermore, it is contemplated that quantitative pulmonary angiography and/or transesophageal echocardiography may provide sufficient diagnostic tools for measuring a patients inter-pulmonary vein ostia distances prior to long linear lesioning treatment. The kit will also typically include appropriate packaging for the individual devices and instructions for operation and use.

In still another procedural aspect of the current invention, patients receiving the long linear lesioning treatment described for the present invention may benefit from the administration of various anticoagulants such as Cumidin and/or Heparin.

It is to be understood from the disclosure above that that particular variations of a broader invention have been described. Additional modifications or variations other than those particularly described may be made based on this disclosure according to one of ordinary skill without departing from the scope of the following claims.

What is claimed is:

1. An apparatus for treating atrial arrhythmia in a patient, comprising:
   (a) an ablation element that is constructed to couple to an ablation actuator and also to be positioned along a region of tissue at least in part at a location where a pulmonary vein extends from an atrium in order to ablate the tissue; and (b) an anchor that is coupled to the ablation element and is constructed to be positioned within the pulmonary vein and that comprises an expandable member that is constructed to expand to a sufficient outer diameter to engage a pulmonary vein wall at an anchoring position along the pulmonary vein such that the ablation element is substantially secured along the location.

2. An apparatus as recited in claim 1, wherein said elongate body has a longitudinal axis, wherein said ablation element has a length located along the longitudinal axis of the elongate body, and wherein said anchor is located along the elongate body generally distal to the ablation element relative to the longitudinal axis.

3. An apparatus as recited in claim 1, wherein the expandable member comprises an inflatable balloon.

4. An apparatus as recited in claim 1, wherein the expandable member comprises a central axis configured to be substantially aligned with and extend along a central longitudinal axis of the pulmonary vein when the expandable member is anchored at the anchoring position and the ablation element extends proximally from the expandable member off center from the central axis.

5. An apparatus as recited in claim 1, further comprising a perfusion passageway that is constructed to allow a volume of blood to flow from a region distally of the expandable member, along the pulmonary vein across the expandable member, and proximally of the expandable member when the expandable member is expanded and engaged to the wall of the pulmonary vein at the anchoring position.

6. An apparatus as recited in claim 5, wherein the perfusion passageway comprises a perfusion lumen extending between a distal port along the distal end portion and a proximal port located proximally of the distal port along the distal end portion, and wherein the expandable member is located along the distal end portion between the distal and proximal ports.

7. An apparatus for treating atrial arrhythmia in a patient, comprising:
(a) an ablation element that is constructed to couple to an ablation actuator and also to be positioned along a region of tissue at least in part at a location where a pulmonary vein extends from an atrium in order to ablate the tissue; and
(b) an anchor that is coupled to the ablation element and is constructed to be positioned within the pulmonary vein, wherein the anchor is further adapted to engage and thereby anchor to a pulmonary vein wall of the pulmonary vein at an anchoring position along the pulmonary vein such that the ablation element is substantially secured along the location.

8. An apparatus as recited in claim 7, further comprising a delivery member with a proximal end portion and a distal end portion which cooperates with the anchor and also with the ablation element at least in part to deliver the anchor to the anchoring position and the ablation element along the location.

9. An apparatus as recited in claim 8, wherein the anchor and ablation element are both located along the distal end portion of the delivery member.

10. An apparatus as recited in claim 8, wherein the ablation element is located at least in part proximally of the anchor with respect to the delivery member.

11. An apparatus as recited in claim 7, wherein the ablation element has a length and is constructed to ablatively couple a region of tissue that extends from the location and along a wall of the atrium.

12. An apparatus as recited in claim 7, wherein the ablation element is moveable relative to the anchor so as to be repositionable at multiple positions along a circumferential path that corresponds to a circumferential region of tissue at the location.

13. An apparatus as recited in claim 7, further comprising a stylet, wherein the ablation element is located along the stylet and the stylet is adapted to position the ablation element along the location for ablation.

14. An apparatus as recited in claim 7, wherein the ablation element comprises an electrical ablation element with at least one electrode which is adapted to couple to an electrical current source.

15. An apparatus as recited in claim 14, when the ablation element comprises a plurality of said electrodes which are spaced along the distal end portion to form a linear ablation element.

16. An apparatus as recited in claim 7, wherein the ablation element comprises a cyroblation element.

17. An apparatus as recited in claim 7, wherein the ablation element comprises a light emitting ablation element.

18. An apparatus a recited in claim 7, wherein the ablation element comprises a microwave ablation element.

19. An apparatus as recited in claim 7, wherein the ablation element comprises a fluid ablation element.

20. An apparatus as recited in claim 7, wherein the ablation element comprises a fluid ablation element.

21. An apparatus as recited in claim 7, wherein the ablation element comprises a thermal ablation element.

22. An apparatus as recited in claim 7, further comprising an ablation actuating assembly which is constructed to couple to and actuate the ablation element.

23. An apparatus as recited in claim 8, wherein said delivery member comprises an elongate body.

24. A tissue ablation device assembly for ablating a region of cardiac tissue in a patient, comprising:
(a) an ablation member, said ablation member having first and second end portions, said ablation member including an ablation element having a length between said first and second end portions of said ablation member, wherein said ablation element is adapted to couple to an ablation actuator; and
(b) an anchor coupled to said first end portion of said ablation member, said anchor including an expandable member that is positionable within a pulmonary vein extending from the left atrial wall of a patient, wherein said expandable member is expandable to a radially expanded condition that is adapted to engage the pulmonary vein;
(c) wherein said ablation element is further adapted to extend along the region of tissue when said expandable member is positioned and engaged within the pulmonary vein in the radially expanded condition.

25. A tissue ablation device assembly as recited in claim 24, wherein said expandable member comprises an inflatable balloon that is adapted to couple to a pressurizeable fluid source and to inflate with fluid from the fluid source to the radially expanded position.

26. A tissue ablation device assembly as recited in claim 24, wherein said anchor further comprises a guidewire tracking member that is adapted to slideably engage and track over a guidewire positioned within the pulmonary vein.

\* \* \* \* \*